US009892521B2

(12) United States Patent
Enomoto

(10) Patent No.: US 9,892,521 B2
(45) Date of Patent: Feb. 13, 2018

(54) RADIATION IMAGE PROCESSING DEVICE AND METHOD, AND RADIOGRAPHIC IMAGING SYSTEM

(71) Applicant: FUJIFILM Corporation, Tokyo (JP)

(72) Inventor: Jun Enomoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 380 days.

(21) Appl. No.: 14/830,105

(22) Filed: Aug. 19, 2015

(65) Prior Publication Data

US 2015/0363926 A1    Dec. 17, 2015

Related U.S. Application Data

(63) Continuation of application No. PCT/JP2014/053721, filed on Feb. 18, 2014.

(30) Foreign Application Priority Data

Feb. 20, 2013  (JP) .................................. 2013-030588

(51) Int. Cl.
  *G06T 7/30* (2017.01)
  *A61B 6/00* (2006.01)
  *G06T 7/33* (2017.01)

(52) U.S. Cl.
  CPC ............. *G06T 7/30* (2017.01); *A61B 6/4233* (2013.01); *A61B 6/463* (2013.01); *A61B 6/486* (2013.01);
  (Continued)

(58) Field of Classification Search
  CPC ... A61B 6/542; A61B 6/544; G06T 7/30–7/38
  See application file for complete search history.

(56) References Cited

U.S. PATENT DOCUMENTS

| 2005/0013471 | A1* | 1/2005 | Snoeren ................... G06T 7/35 382/131 |
| 2007/0238963 | A1 | 10/2007 | Kaminaga et al. |
| 2010/0119033 | A1* | 5/2010 | Li ........................... A61B 6/06 378/5 |

FOREIGN PATENT DOCUMENTS

| JP | 7-201490 A | 8/1995 |
| JP | 2002-590 A | 1/2002 |

(Continued)

OTHER PUBLICATIONS

Ruchala, Kenneth J., et al. "Methods for improving limited field-of-view radiotherapy reconstructions using imperfect a priori images." Medical physics 29.11 (2002): 2590-2605.*
Chinese Office Action issued in Chinese Application No. 201480009697.7 dated Jun. 27, 2017, with an English translation.
International Search Report issued in PCT/JP2014/053721, dated May 13, 2014.

(Continued)

*Primary Examiner* — Stephen R Koziol
*Assistant Examiner* — Raphael Schwartz
(74) *Attorney, Agent, or Firm* — Birch, Stewart, Kolasch & Birch, LLP

(57) ABSTRACT

A console structure in an X-ray imaging system performs image processing of plural radiation images formed by an X-ray imaging apparatus having an active pixel area with pixels for detecting a radiation image of a body. The plural radiation images are formed by imaging one object in the body with a time interval. The console structure acquires the radiation images. An information controller obtains field information of a position of an exposure field which is associated with each one of the radiation images and automatically set in the active pixel area according to a position of the body being positioned for automatic exposure control in the X-ray imaging apparatus before imaging. A matching unit performs position matching according to the field information to match the position of the body in the plural (Continued)

radiation images between plural display images corresponding to respectively the plural radiation images.

15 Claims, 24 Drawing Sheets

(52) U.S. Cl.
CPC ............ *A61B 6/5205* (2013.01); *A61B 6/542* (2013.01); *A61B 6/545* (2013.01); *A61B 6/589* (2013.01); *G06T 7/33* (2017.01); *G06T 2200/24* (2013.01); *G06T 2207/10016* (2013.01); *G06T 2207/10116* (2013.01); *G06T 2207/10144* (2013.01); *G06T 2207/20221* (2013.01); *G06T 2207/30061* (2013.01)

(56) References Cited

FOREIGN PATENT DOCUMENTS

| | | |
|---|---|---|
| JP | 2003-159240 A | 6/2003 |
| JP | 2007-167634 A | 7/2007 |
| JP | 2011-10870 A | 1/2011 |

OTHER PUBLICATIONS

Written Opinion of the International Searching Authority issued in PCT/JP2014/053721, dated May 13, 2014.

\* cited by examiner

FIG.2

| OBJECT (BODY PART) | TUBE VOLTAGE (kV) | TUBE CURRENT (mA) | IRRADIATION TIME (s) | STOP THRESHOLD |
|---|---|---|---|---|
| ⋮ | ⋮ | ⋮ | ⋮ | ⋮ |
| CHEST AP | VAP | IAP | TAP | thAP |
| CHEST PA | VPA | IPA | TPA | thPA |
| ⋮ | ⋮ | ⋮ | ⋮ | ⋮ |

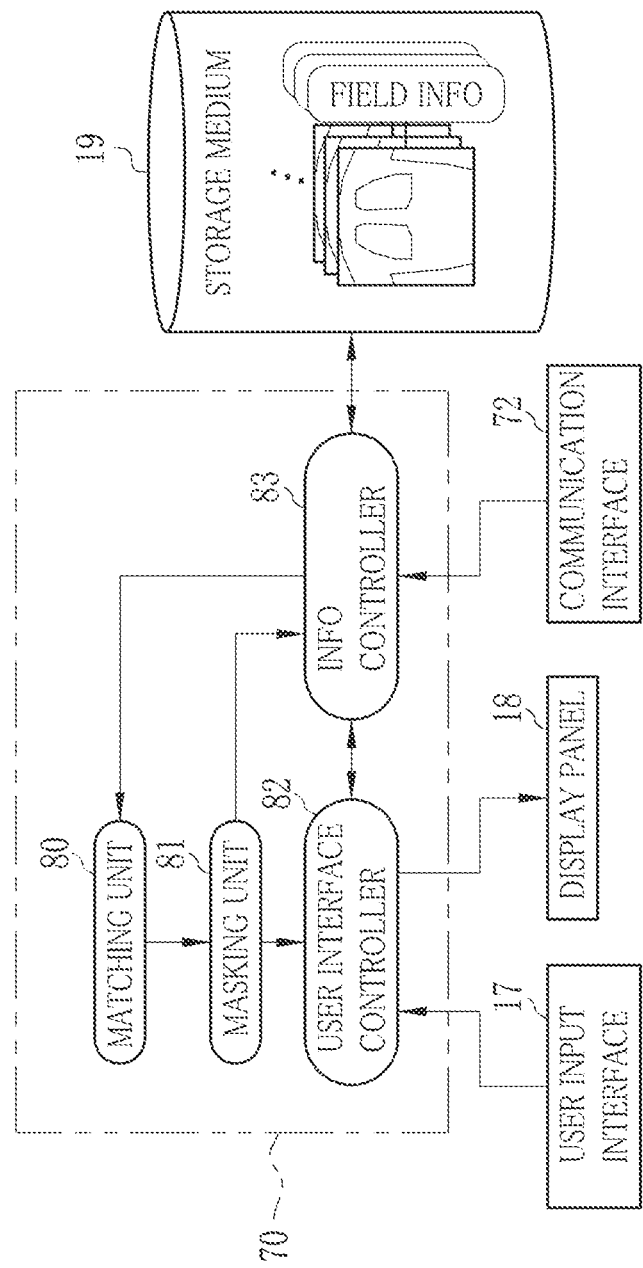

FIG. 14A
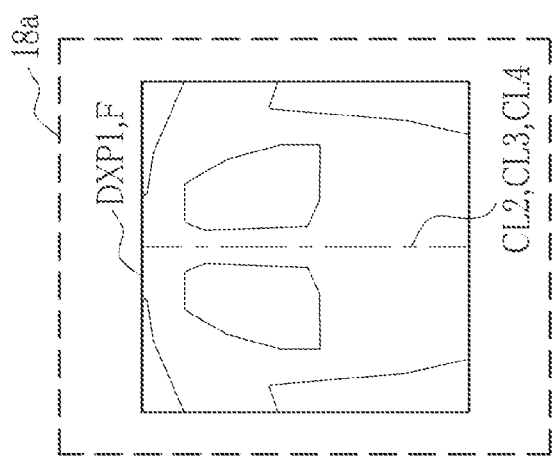
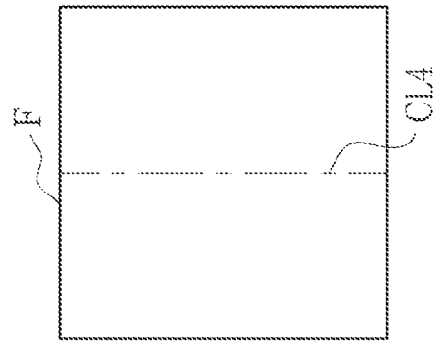
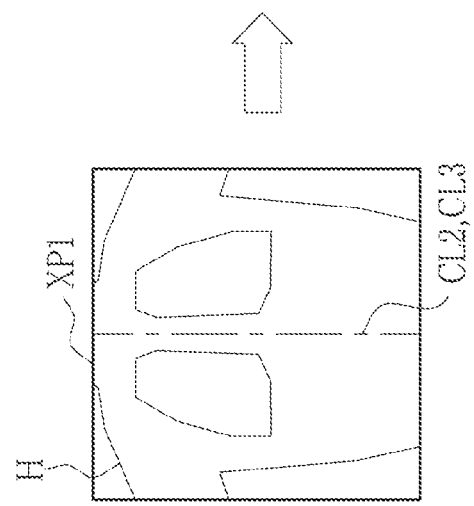

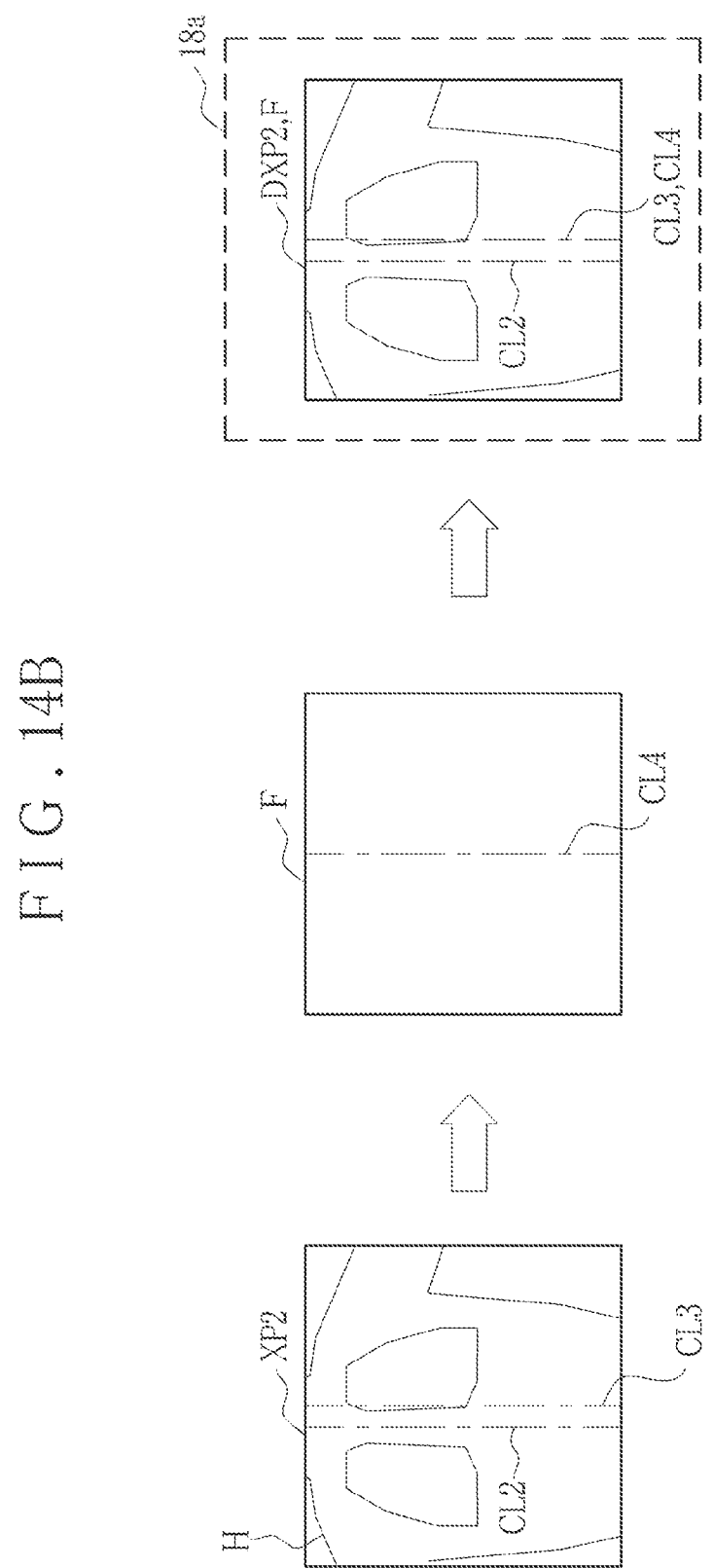

RADIATION IMAGE PROCESSING DEVICE AND METHOD, AND RADIOGRAPHIC IMAGING SYSTEM

CROSS-REFERENCE TO RELATED APPLICATION

This application is a Continuation of PCT International Application PCT/JP2014/053721 filed on 18 Feb. 2014, which claims priority under 35 USC 119(a) from Japanese Patent Application No. 2013-030588 filed on 20 Feb. 2013. The above application is hereby expressly incorporated by reference, in its entirety, into the present application.

BACKGROUND OF THE INVENTION

1. Field of the Invention

The present invention relates to a radiation image processing device and method and a radiographic imaging system. More particularly, the present invention relates to a radiation image processing device and method and a radiographic imaging system, in which an exposure field is automatically set in the course of imaging, and in which a display image suitable for image interpretation can be obtained in a simple structure.

2. Description Related to the Prior Art

An X-ray imaging system or radiographic imaging system in which X-rays are used is well-known in the field of medical diagnosis. The X-ray imaging system includes an X-ray source apparatus or radiation source apparatus, and an X-ray imaging apparatus or radiographic imaging apparatus. The X-ray source apparatus generates X-rays. The X-ray imaging apparatus forms a radiation image or X-ray image by detecting X-rays transmitted through a body of a patient. The X-ray source apparatus includes an X-ray source, a controllable source driver and a radiation switch. The X-ray source emits X-rays to the object. The source driver controls operation of the X-rays source. The radiation switch sends an input signal to the source driver for starting the X-ray source. The X-ray imaging apparatus includes an electronic cassette or X-ray image detector, and a console structure. The electronic cassette detects the radiation image according to X-rays from the object. The console structure controls the electronic cassette, processes the radiation image for image processing, and performs storing processing and display processing of the radiation image.

The electronic cassette has a sensor panel or sensor matrix, which is referred to as an FPD or flat panel detector, and detects the radiation image electronically. An active pixel area of the sensor panel includes a great number of pixels for storing signal charge according to a dose of incident X-rays. Each of the pixels includes a photoconductor for generating and storing charge, and a switching element such as a TFT. In case the switching element is turned on, the sensor panel reads out the signal charge into a signal processing circuit from the photoconductor of each pixel through a signal line disposed for each of arrays of the pixels. The signal processing circuit converts the signal charge into a voltage signal to detect the radiation image electrically.

In the X-ray imaging system, the use of AEC (automatic exposure control) is known. For the purpose of forming the radiation image with an appropriate quality with a reduced dose of X-rays to the object or a body, a dose of X-rays is detected during irradiation of the X-rays, to stop the irradiation of the X-ray source upon reach of a cumulative dose of X-rays to a target dose. The cumulative dose of the X-rays from the X-ray source is determined according to a tube current-time product (in the unit of mA·s) obtained by multiplication of irradiation time of X-rays by a tube current determining the dose of X-rays per unit time. In general, each of imaging conditions including the irradiation time and tube voltage has recommended values with differences in compliance with body parts, sex, age and other specifics of a body or object, the body parts including a chest, head and the like. However, the use of AEC is important for obtaining improved image quality because transmittance of X-rays differs according to specificity of the body, for example, a body size.

A monitoring device or AEC device for detecting a dose of X-rays transmitted through an object is used for the AEC. A known example of the monitoring device is an ionization chamber for combined use with the electronic cassette. The ionization chamber includes monitoring sensors, two of which are disposed at two upper points in compliance with right and left lungs in imaging of the chest, and one of which is disposed under the two upper points. The ionization chamber is so disposed as to cover a front or rear surface of the electronic cassette. For example, the upper two of the monitoring sensors are selected as an exposure field (receiving field) as a reference of monitoring in the AEC before the imaging of the chest. Then the object is positioned for relative positioning with the electronic cassette to oppose the right and left lungs of the body to the selected exposure field. Assuming that the positioning is incorrect, the AEC cannot be performed correctly due to an offset between the right and left lungs and the exposure field. The positioning must be exact. After completing operation of the positioning, the imaging is started. In the imaging, a time point of stopping irradiation of X-rays is obtained according to a dose signal output by the monitoring sensors selected as the exposure field.

JP-A 7-201490 and JP-A 2002-000590 disclose a structure including the sensor panel and the monitoring device combined with the sensor panel. The sensor panel of the documents has pixels which operate as the monitoring sensors within the active pixel area for detecting the radiation image. Any of the pixels can be manually designated as the exposure field. For the AEC by use of the monitoring in the sensor panel according to this disclosure, the exposure field is selected prior to the imaging and an object is positioned in compliance with the selected exposure field, in a manner similar to the use of the ionization chamber. Then the imaging is started.

Automation of setting the exposure field in the course of imaging has been technically conceived as a development of the disclosure in JP-A 7-201490 and JP-A 2002-000590 in which pixels of the sensor panel are used as the monitoring sensors. Part of the pixels in the sensor panel are used as monitoring pixels for operation as the monitoring sensors. The monitoring pixels are arranged within the active pixel area in a discrete manner. The exposure field is determined according to the dose signal output by the monitoring pixels. For example, one of the monitoring pixels opposed to the right and left lungs in the chest imaging generates a higher output than those opposed to other body parts adjacent to the right and left lungs. Thus, the monitoring pixels with the higher output than the other monitoring pixels are automatically set as the exposure field. Then the monitoring pixels of the exposure field are used for the AEC according to the dose signal. As a result, it is technically unnecessary to select the exposure field conventionally required for preparatory operation. Also, strictly high precision in the positioning of the object is unnecessary because the exposure field is automatically set according to the relative position between the object and the electronic cassette.

In image diagnosis of the medical field, a plurality of the radiation images formed by imaging the same body part in plural events with a time interval is read and interpreted in comparison as observation of the progress, for example, images before and after surgery. The radiation images are arranged and displayed in a screen view of a display panel, or displayed respectively in a manner changeable over one after another. The radiation images are displayed suitably for image interpretation in comparison.

For example, an object in the radiation image before surgical operation is disposed approximately at the center. However, the object after the surgical operation may be offset toward the right or left in the radiation image. The image interpretation in comparison is difficult upon occurrence of a change in the position of the object between the plural radiation images. It is preferable that a position of the object in the radiation images is constant between the radiation images for use in the observation of the progress.

Assuming that the automated setting of the exposure field in the course of imaging is used, no precision in the positioning the object in the conventional technique is necessary. However, a relative position between an object and the electronic cassette is unequal between images obtained from plural events of imaging for the purpose of the observation of the progress. A problem arises in a difference in the position of an object between the radiation images.

To cope with this problem, the radiation images are analyzed in image analysis such as pattern analysis to recognize a position of the object in the radiation images. Position matching is performed to match the position of the object between the radiation images according to the recognized position. However, the image analysis method of recognizing the position of the object in the radiation images requires complicated processing and long time. There is no known solution of a simple form in relation to the above-described problem.

SUMMARY OF THE INVENTION

In view of the foregoing problems, an object of the present invention is to provide a radiation image processing device and method and a radiographic imaging system, in which an exposure field is automatically set in the course of imaging, and in which a display image suitable for image interpretation can be obtained in a simple structure.

In order to achieve the above and other objects and advantages of this invention, a radiation image processing device performs image processing of plural radiation images formed by a radiographic imaging apparatus having an active pixel area with plural pixels for detecting a radiation image of a body, the plural radiation images being formed by imaging one object in the body in plural imaging events with a time interval. The radiation image processing device includes an image acquisition unit for acquiring the radiation images. An information controller obtains field information of a position of an exposure field which is associated with each one of the radiation images and automatically set in the active pixel area according to a position of the body being positioned for automatic exposure control in the radiographic imaging apparatus before imaging. A matching unit performs position matching according to the field information from the information controller to match the position of the body in the plural radiation images between plural display images corresponding to respectively the plural radiation images.

Preferably, the matching unit matches the position of the exposure field between the plural radiation images to match the position of the body between the plural display images.

Preferably, the field information is coordinate information of a position of the exposure field in the radiation image.

In another preferred embodiment, the matching unit obtains a reference point of positioning within the exposure field for the position matching.

Preferably, the reference point is a center of a quadrilateral frame disposed around the exposure field and tangential to a peripheral line of the exposure field.

Preferably, the matching unit selects a reference image from among the plural radiation images, and performs the position matching with reference to a position of the exposure field of the reference image.

Preferably, the reference image is one selected radiation image selected among the radiation images by manual or automatic selection.

Preferably, the matching unit performs the position matching by shifting an arrangement position of the display image relative to a display frame for arranging the display image.

Preferably, furthermore, there is a masking unit for masking of a blank portion formed in the display frame by a shift of the arrangement position.

Preferably, furthermore, a storage medium stores an amount of a shift of the display images after the position matching or a shift of the arrangement position in the position matching, in association with the radiation images.

Preferably, the field information is expressed by use of pixel addresses of pixels among the pixels corresponding to the exposure field within the radiation images.

Preferably, the radiographic imaging apparatus includes a sensor panel having the active pixel area. A plurality of monitoring sensors are disposed in the active pixel area discretely from one another, for detecting a dose of radiation incident upon the active pixel area to output a dose signal of the dose. A field setting unit automatically sets the exposure field according to the dose signal from the monitoring sensors during imaging. An AEC device performs the automatic exposure control according to the dose signal from at least one of the monitoring sensors disposed in the exposure field set by the field setting unit.

Also, a radiation image processing method is provided for image processing of plural radiation images formed by a radiographic imaging apparatus having an active pixel area with plural pixels for detecting a radiation image of a body, the plural radiation images being formed by imaging one object in the body in plural imaging events with a time interval. In the radiation image processing method, the radiation images are acquired. Field information of a position of an exposure field is obtained, the exposure field being associated with each one of the radiation images and automatically set in the active pixel area according to a position of the body being positioned for automatic exposure control in the radiographic imaging apparatus before imaging. Position matching is performed according to the field information to match the position of the body in the plural radiation images between plural display images corresponding to respectively the plural radiation images.

Also, a radiographic imaging system is provided, including a radiographic imaging apparatus having an active pixel area with plural pixels for detecting a radiation image of a body, and a radiation image processing device for image processing of plural radiation images formed by the radiographic imaging apparatus imaging one object in the body in plural imaging events with a time interval. In the radiographic imaging system, the radiation image processing device includes an image acquisition unit for acquiring the radiation images. An information controller obtains field information of a position of an exposure field which is associated with each one of the radiation images and automatically set in the active pixel area according to a position of the body being positioned for automatic exposure control in the radiographic imaging apparatus before imaging. A matching unit performs position matching according to the field information from the information controller to match the position of the body in the plural radiation images between plural display images corresponding to respectively the plural radiation images.

Preferably, the radiographic imaging apparatus includes a sensor panel having the active pixel area. A plurality of monitoring sensors are disposed in the active pixel area discretely from one another, for detecting a dose of radiation incident upon the active pixel area to output a dose signal of the dose. A field setting unit automatically sets the exposure field according to the dose signal from the monitoring sensors during imaging. An AEC device performs the automatic exposure control according to the dose signal from at least one of the monitoring sensors disposed in the exposure field set by the field setting unit.

Accordingly, a display image suitable for image interpretation can be obtained in a simple structure, because field information of an exposure field is utilized for position matching to match a position of a body between the plural display images.

BRIEF DESCRIPTION OF THE DRAWINGS

The above objects and advantages of the present invention will become more apparent from the following detailed description when read in connection with the accompanying drawings, in which:

FIG. 2 is a table illustrating an imaging condition data table;

FIG. 12 is a block diagram illustrating a CPU in the console structure;

FIG. 14A is an explanatory view illustrating display processing of a display image corresponding to FIG. 13A;

FIG. 14B is an explanatory view illustrating display processing of a display image corresponding to FIG. 13B;

DETAILED DESCRIPTION OF THE PREFERRED EMBODIMENT(S) OF THE PRESENT INVENTION

Figure 1:
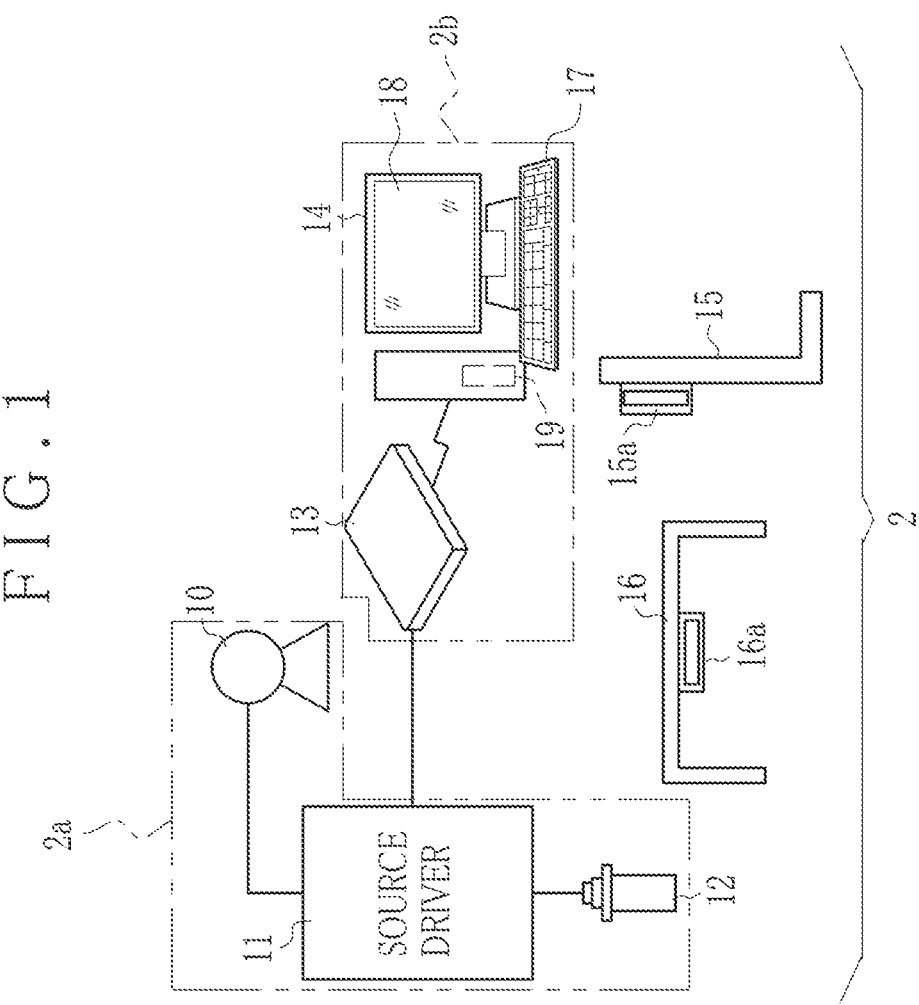
FIG. 1 is an explanatory view illustrating an X-ray imaging system.

In FIG. 1, an X-ray imaging system 2 as a radiographic imaging system includes an X-ray source 10, a source driver 11 or source control unit, a radiation switch 12, an electronic cassette 13 (X-ray image detector), a console structure 14 or user terminal device as radiation image processing device, a floor stand 15 and a patient table 16. The source driver 11 controls the X-ray source 10. The radiation switch 12 inputs signals for starting warmup of the X-ray source 10 and starting irradiation of X-rays. The electronic cassette 13 has a function of AEC for stopping irradiation of X-rays upon reach of a cumulative dose of X-rays to a target dose, detects X-rays transmitted through a body of a patient, and outputs a radiation image (X-ray image). The console structure 14 controls operation of the electronic cassette 13 and performs display processing of the radiation image. The floor stand 15 is used for imaging of the body in a vertical posture. The patient table 16 is used for imaging of the body in a horizontal posture. An X-ray source apparatus 2a is constituted by the X-ray source 10, the source driver 11 and the radiation switch 12. An X-ray imaging apparatus 2b as a radiographic imaging apparatus is constituted by the electronic cassette 13 and the console structure 14. Also, a source moving mechanism (not shown) is disposed to set the X-ray source 10 in a direction and position according to a user's intention. The X-ray source 10 is used commonly with the floor stand 15 and the patient table 16.

The X-ray source 10 includes an X-ray tube and a collimator for limiting a radiation field of X-rays from the X-ray tube. The X-ray tube includes a negative electrode and a positive electrode (target). The negative electrode is a filament for emitting thermal electron. The positive electrode emits X-rays upon collision with the thermal electron from the negative electrode. Upon receiving the command for starting the warmup, the positive electrode starts rotation. In case a rotational speed of the rotation becomes equal to a predetermined speed, the warmup is completed. The collimator includes four blocking plates of metal lead. The blocking plates are arranged quadrilaterally for blocking X-rays. A radiation opening is defined between the blocking plates at the center. Shifting the blocking plates changes a size of the radiation opening, to adjust an angular range of X-rays in both of horizontal and vertical directions. Thus, the radiation field can be controlled and limited.

The console structure 14 is set communicable with the electronic cassette 13 by wired or wireless communication. A user input interface 17, such as a keyboard or other input devices, is used by a user or operator (doctor or technician of radiology) to input signals to control the electronic cassette 13. A display panel 18 of the console structure 14 is driven to display radiation images from the electronic cassette 13. Image data of the radiation images are stored in a storage medium 19 or storage device, such as a hard disk drive or memory in the console structure 14, or an image server in connection with the console structure 14 by network connection.

The console structure 14 receives a medical request for examination with information of attributes, such as name, sex, age, and body part of the patient as body, and a purpose of imaging. The console structure 14 drives the display panel 18 to display the medical request. Various methods are available for inputting the medical request. For example, an external system for managing case information and condition information can input the medical request, for example, HIS (Hospital Information System) and RIS (Radiology Information System). Also, an operator may manually input the medical request. Examples of the body parts include a head, chest, abdomen, hands, fingers and the like. Also, information of viewing directions can be added to the body parts, such as a front direction, lateral direction and diagonal direction, and a PA (posteroanterior) direction and AP (anteroposterior) direction for irradiation. An operator views various data in the medical request for examination on the display panel 18, and manipulates the user input interface 17 to input an imaging condition by referring to the items on the display panel 18.

In FIG. 2, an imaging condition data table 20 is stored in the storage medium 19, and has information of plural predetermined imaging conditions. Each one of the imaging conditions has a body part, tube voltage, tube current, irradiation time (in the unit of second) and stop threshold. The tube voltage (in the unit of kV) is a value determining energy spectrum of X-rays to be emitted by the X-ray source 10. The tube current (in the unit of mA) is a value determining dose per unit time. A cumulative dose of X-rays is a product of multiplication of the tube current and irradiation time. Thus, it is possible to input a tube current-time product (in the unit of mA·s) instead of discretely inputting values of the tube current and irradiation time for the imaging condition. Note that the tube voltage, tube current and irradiation time can be adjusted finely. The stop threshold is information with which an AEC device 57 or monitoring device checks a stop of irradiation of X-rays. See FIG. 5. In FIG. 2, only the chest in the direction AP and the chest in the direction PA are illustrated as a body part. However, imaging conditions are predetermined also for other body parts, such as head, abdomen, legs and the like, and for stop thresholds in association with those body parts.

Various data are input to the console structure 14 by use of the user input interface 17, including the imaging condition, angular ranges of X-rays in horizontal and vertical directions at the collimator of the X-ray source 10, and a SID (source-image distance) as a distance between a position of an active pixel area 40 of the electronic cassette 13 (See FIG. 5) and a focal point of the X-ray tube.

Figure 3:
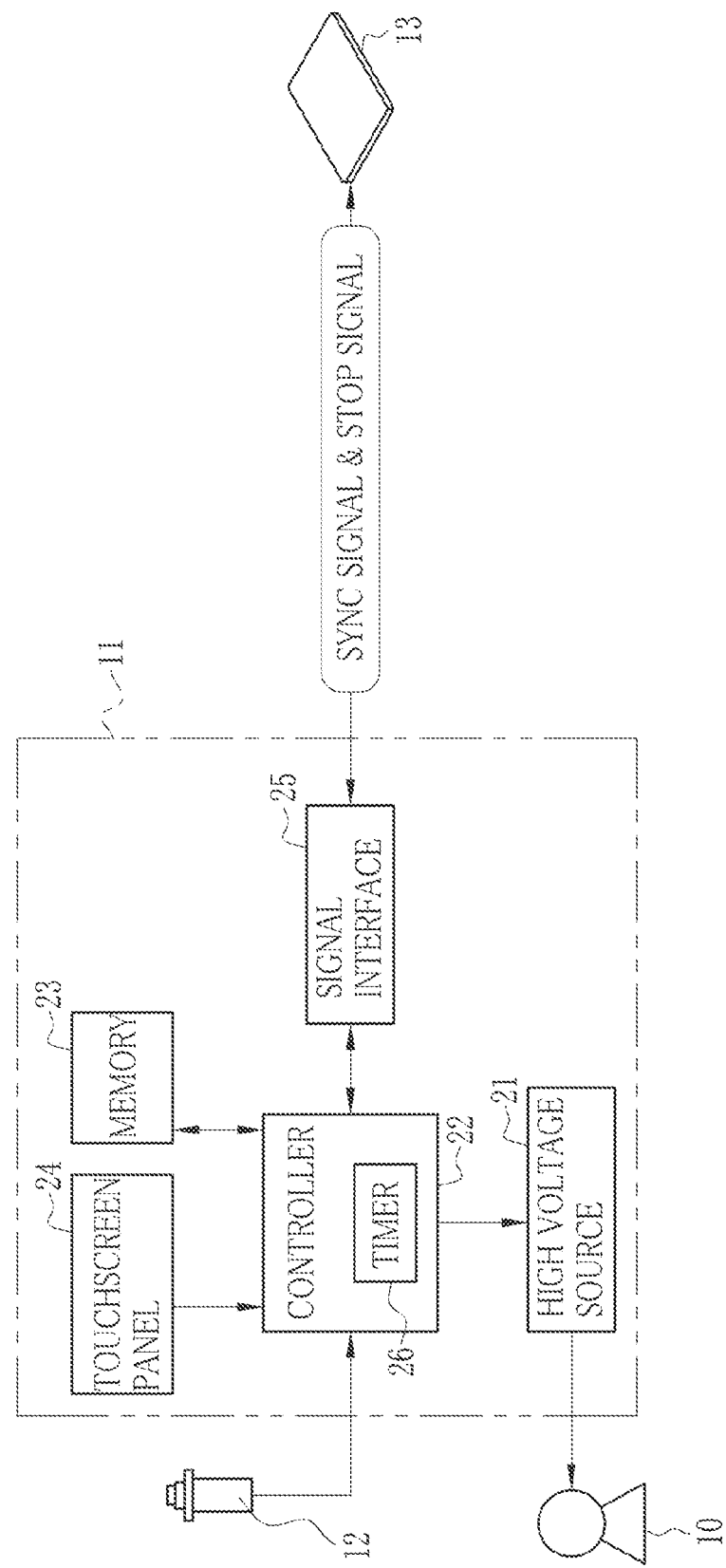
FIG. 3 is a block diagram illustrating a source driver.

In FIG. 3, the source driver 11 includes a high voltage source 21, a controller 22, a memory 23, a touchscreen panel 24 and a signal interface 25 for an irradiation signal. The high voltage source 21 generates an high tube voltage by boosting an input voltage in a transformer, and supplies the X-ray source 10 with the high tube voltage through a high voltage cable. The controller 22 controls the tube voltage and tube current for the X-ray source 10, and controls irradiation time of X-rays. The signal interface 25 sends or receives signals with the electronic cassette 13.

To the controller 22 are connected the radiation switch 12, the memory 23 and the touchscreen panel 24. The radiation switch 12 is for inputting a command signal to the controller 22, and is depressible in two steps of depth. In case the radiation switch 12 is depressed halfway or at a first step, the controller 22 transmits a start signal for warmup to the high voltage source 21, for the X-ray source 10 to start the warmup.

In case the radiation switch 12 is depressed halfway or at a first step of depth, the controller 22 performs sync control by sending and receiving a sync signal with the electronic cassette 13. In case the radiation switch 12 is depressed fully or at a second step of depth, the controller 22 sends a start signal to the high voltage source 21 to start irradiation of X-rays of the X-ray source 10.

The memory 23 stores a plurality of imaging conditions each of which includes a tube voltage, tube current, irradiation time and the like. To input a selected one of the imaging conditions, the touchscreen panel 24 is manually operated by a user or operator. The touchscreen panel 24 displays the plural types of imaging conditions read out from the memory 23. A user or operator selects one of the displayed imaging conditions equal to that input to the console structure 14, to set the imaging condition to the source driver 11. In a manner similar to the console structure 14, values of the imaging condition are adjustable finely. A timer 26 is incorporated in the controller 22 for stopping irradiation of X-rays at the predetermined irradiation time. It is also possible to connect the console structure 14 with the source driver 11, and automate input of the imaging condition in the source driver 11 by transmitting the input imaging condition to the source driver 11.

Irradiation time for the AEC in the electronic cassette 13 is predetermined sufficiently long for the purpose of preventing shortage in the dose, because the irradiation of X-rays must not be stopped before detecting the reach to the target dose for stopping the irradiation in the AEC. An example of the irradiation time can be a maximum irradiation time in view of the safety regulation in the X-ray source 10. The controller 22 performs control of the X-ray irradiation according to the tube voltage, tube current and irradiation time of the determined imaging condition. Assuming that it is judged that the cumulative dose of X-rays has come up to the target dose of sufficiency, the AEC functions to stop the X-ray irradiation even in case the measured time is equal to or less than the irradiation time set in the source driver 11.

The signal interface 25 sends and receives a sync signal in the course of sync control between the source driver 11 and the electronic cassette 13. Before starting X-ray irradiation, the controller 22 transmits a request signal to the electronic cassette 13 through the signal interface 25 by way of a sync signal to ask for allowance of starting the X-ray irradiation. The controller 22 receives an allowance signal from the electronic cassette 13 as a sync signal representing readiness for receiving the irradiation as a response to the request signal. In case the electronic cassette 13 performs the AEC, the controller 22 receives a stop signal from the electronic cassette 13 for stopping the irradiation. Note that a method of communication of the signal interface 25 can be both wired and wireless.

Figure 4:
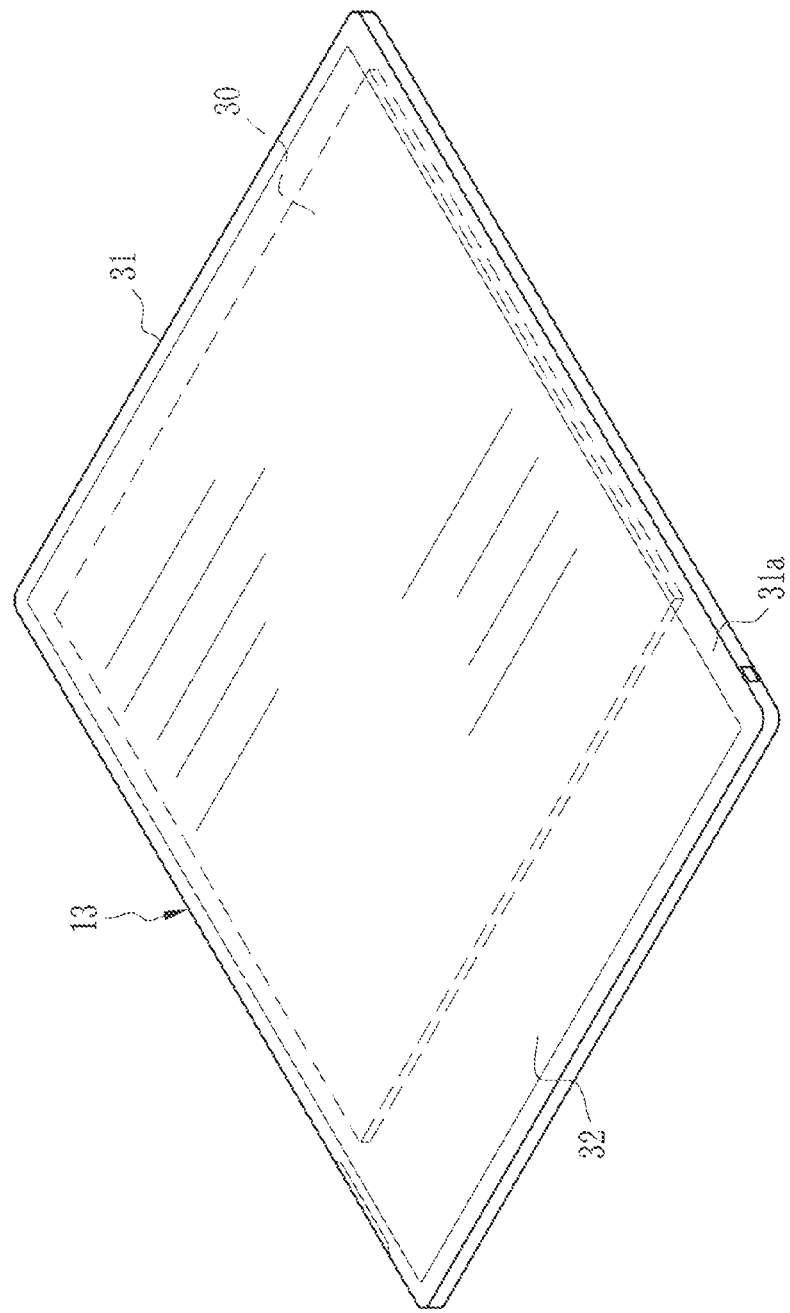
FIG. 4 is a perspective view illustrating an electronic cassette.

In FIG. 4, the electronic cassette 13 includes a sensor panel 30 and a portable housing 31 of a box shape of a small thickness. An example of material of the portable housing 31 is electrically conductive resin. The portable housing 31 has an imaging surface 31a or front surface, a quadrilateral aperture opening, and a transparent plate 32. The aperture opening is formed in the imaging surface 31a for receiving X-rays. The transparent plate 32 closes the aperture opening as a top plate. The transparent plate 32 is formed from a carbon material which has a small weight, high rigidity, and is highly radio-transparent to X-rays. The portable housing 31 as an electromagnetic shield prevents entry of electromagnetic noise toward the electronic cassette 13, and prevents propagation of electromagnetic noise toward the outside of the electronic cassette 13. Furthermore, a battery and an antenna are contained in the portable housing 31 in addition to the sensor panel 30. The battery is a secondary cell for supplying various elements of the electronic cassette 13 with power at a predetermined voltage. The antenna functions for radio communication with data of X-ray images in connection with the console structure 14.

The portable housing 31 has a size according to the International Standards ISO 4090:2001 in a manner of a film cassette, IP cassette and the like. Cassette holders 15a and 16a are disposed in the floor stand 15 and the patient table 16 in FIG. 1. The electronic cassette 13 is removably set in each one of the cassette holders 15a and 16a so that the imaging surface 31a of the portable housing 31 in the electronic cassette 13 is directed to the X-ray source 10 and that a radiation field of X-rays is kept concentric with the active pixel area 40. The source moving mechanism moves the X-ray source 10 according to one of the floor stand 15 and the patient table 16 for use. Also, the electronic cassette 13 is usable discretely without the use of the floor stand 15 or the patient table 16, for example, can be placed on the bed of the patient or manually held by the patient for imaging. As the size of the electronic cassette 13 is approximately equal to that of the film cassette and IP cassette, the electronic cassette 13 can be mounted on a holder of a known type for the film cassette and IP cassette.

Figure 5:
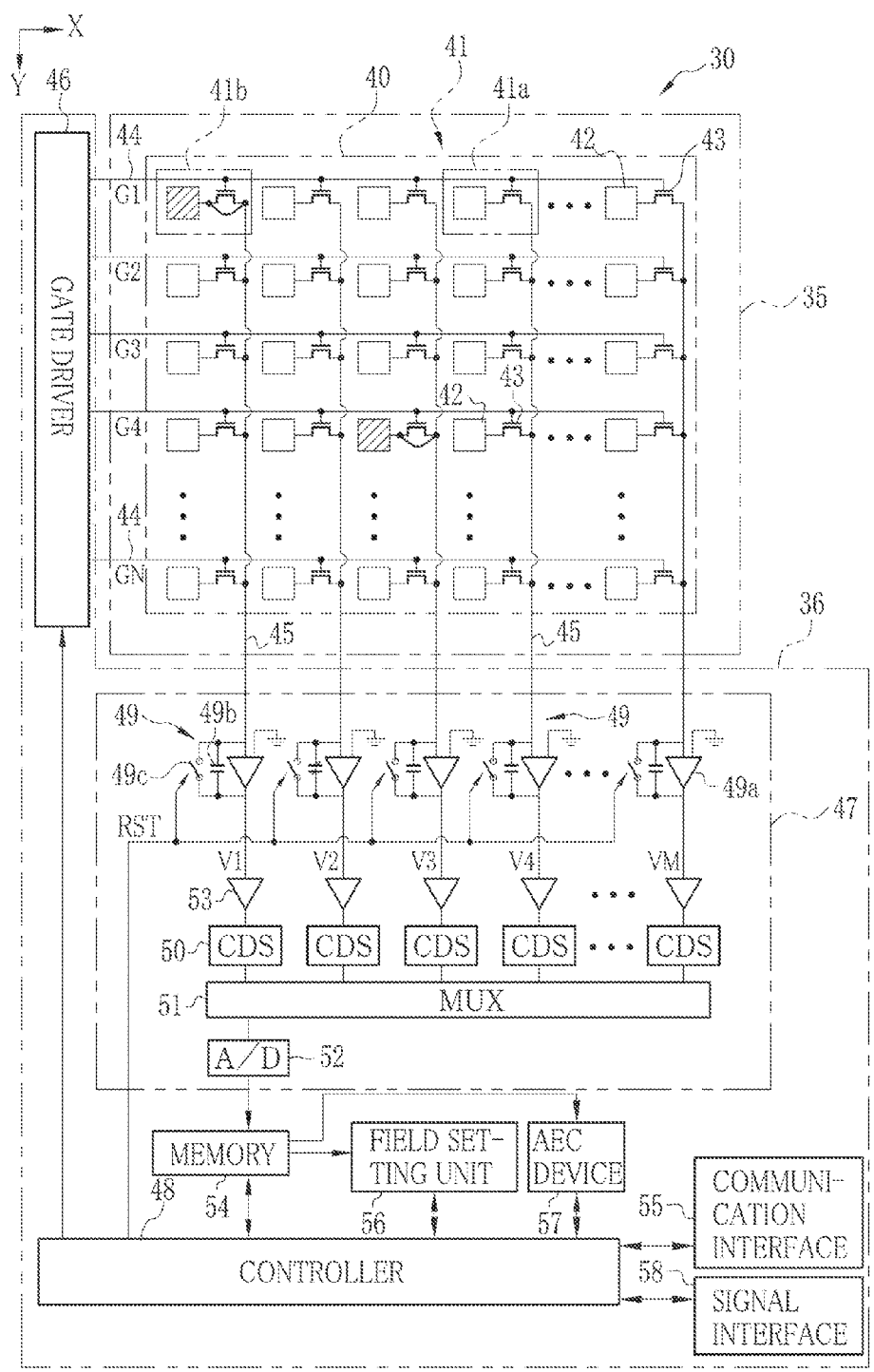
FIG. 5 is a block diagram illustrating the electronic cassette.

In FIG. 5, the sensor panel 30 includes a sensor matrix 35 or panel device or panel board, and a circuit board 36 or circuit device. The sensor matrix 35 has a TFT active matrix substrate where the active pixel area 40 is formed. Pixels 41 are arranged on the active pixel area 40 for storing charge according to dose of received X-rays in plural a matrix form of N arrays and M columns (N×M) at a regular pitch. N and M are integers equal to or more than 2, and for example, are approximately equal to 2,000. Note that arrangement of the pixels 41 is not limited to the regular rectangular arrangement of the embodiment, but can be a honeycomb arrangement.

The sensor matrix 35 includes a scintillator or phosphor (not shown) for converting X-rays into visible light. The sensor matrix 35 is an indirect conversion type in which the pixel 41 receives the visible light from the scintillator, and converts this into a signal photoelectrically. Examples of the scintillator are thallium-activated cesium iodide (CsI:Tl), terbium-activated gadolinium oxysulfide ($Gd_2O_2S$:Tb or GOS), and the like. The scintillator is disposed to face the entire surface of the active pixel area 40 having the pixels 41. Disposition of the scintillator and the TFT active matrix substrate can be according to a PSS method (penetration side sampling method) in which the scintillator is positioned upstream of the substrate, or according to a ISS method (irradiation side sampling method) in which the substrate is positioned upstream of the scintillator. Furthermore, the scintillator may not be used. The sensor matrix 35 can be a direct conversion type in which a conversion layer of amorphous selenium or the like converts X-rays into electric charge directly.

The pixels 41 include photoconductors 42 and thin film transistors 43 or TFTs as well-known in the art. The photoconductors 42 receive visible light, generates charge (electron-hole pair), and stores the charge. The thin film transistors 43 are switching elements.

The photoconductors 42 have a semiconductor layer (for example, PIN) for generating charge, and upper and lower electrodes disposed so that the semiconductor layer is positioned between those. The thin film transistors 43 are connected to the lower electrode of the photoconductors 42. Bias lines are connected to the upper electrode. The number of the bias lines is the number N of arrays of the pixels 41. A parent line is connected with the bias lines. A bias power source is connected with the parent line. A bias voltage is applied to the upper electrode of the photoconductors 42 by the bias power source through the parent line and the bias lines as auxiliary lines. An electric field is created in the semiconductor layer by the bias voltage. Charge from the semiconductor layer (electron-hole pair) according to photoelectric conversion moves to the upper and lower electrodes having positive and negative polarities, so as to store charge in the photoconductors 42.

There are a scan line 44 and a signal line 45. A gate of the thin film transistors 43 is connected to the scan line 44. A source of the thin film transistors 43 is connected to the signal line 45. A drain of the thin film transistors 43 is connected to the photoconductors 42. The scan line 44 and the signal line 45 are wired in arrangement of a grating. The number of the scan lines 44 is N or the number of the arrays of the pixels 41, one of the scan lines 44 being associated with one array. The number of the signal lines 45 is M or the number of the columns of the pixels 41, one of the signal lines 45 being associated with one column. A gate driver 46 is connected with the scan line 44. A signal processor 47 is connected with the signal line 45.

The circuit board 36 includes a controller 48 with the gate driver 46 and the signal processor 47. The gate driver 46 is controlled by the controller 48 and drives the thin film transistors 43, so that the sensor panel 30 is caused to perform a task of storing signal charge in the pixels 41 according to a dose of received X-rays, a task of reading out the stored signal charge from the pixels 41, and a task of pixel reset. In the storing, the thin film transistors 43 are turned off, while the signal charge is stored in the pixels 41. In the readout, the gate driver 46 successively generates gate pulses G1-GN for driving the thin film transistors 43 of one array together at a predetermined interval, to activate the scan line 44 one array after another. The thin film transistors 43 in connection with the scan line 44 are turned on by one array. The charge stored in the photoconductors 42 of the pixels 41 is readout to the signal lines 45 upon turning on the thin film transistors 43, and is input to the signal processor 47.

Dark current charge is generated in the semiconductor layer of the photoconductors 42 irrespective of entry of X-rays. As the bias voltage is applied, the dark current charge is stored in the photoconductors 42 of the pixels 41. A noise component to image data is created by the dark current charge at the pixels 41. To eliminate the noise component, pixel reset of the pixels 41 is performed at a predetermined interval before irradiation of X-rays. The pixel reset is to sweep out the dark current charge from the pixels 41 through the signal line 45.

An example of a method of the pixel reset is a method of successive reset for resetting the pixels 41 by one array. In the successive reset, the gate pulses G1-GN are successively generated at the predetermined interval from the gate driver 46 to the scan lines 44, to turn on the thin film transistors 43 by one array.

Various pixel reset methods can be used in place of the sequential reset, for example, a parallel reset method in which pixels are grouped in groups having plural arrays, and pixels of each group are reset sequentially, to sweep out dark current charge of the arrays of the groups simultaneously, and a total pixel reset method in which gate pulses are simultaneously input to all of the arrays to sweep out dark current charge of all the pixels simultaneously. The pixel reset can be performed at a high speed by use of the parallel reset method or total pixel reset method.

The signal processor 47 includes an integration amplifier 49 or amplifier unit, a CDS device 50 (correlated double sampling device), a multiplexer 51 (MUX) and an A/D converter 52. The integration amplifier 49 is connected to the signal line 45 discretely. The integration amplifier 49 includes an operation amplifier 49a and a capacitor 49b, which is connected between an input and output of the operation amplifier 49a. The signal line 45 is connected to one of the inputs of the operation amplifier 49a. A second input of the operation amplifier 49a is grounded (GND) or earthed. A reset switch 49c is connected in parallel with the capacitor 49b. The integration amplifier 49 integrates charge input from the signal line 45, and converts the charge into voltage signals V1-VM in an analog form.

The multiplexer 51 is connected to outputs of the operation amplifier 49a together with an amplifier 53 and the CDS device 50. The A/D converter 52 is connected to an output of the multiplexer 51. The CDS device 50 has a sample-hold circuit, and eliminates a kTC noise component of the integration amplifier 49 by correlated double sampling of an output voltage of the integration amplifier 49. Also, the sample hold circuit holds the voltage signal from the integration amplifier 49 for a predetermined period. The multiplexer 51 operates according to a control signal from a shift register (not shown), selects one CDS device 50 by use of an electronic switch among the CDS devices 50 of each of the columns parallel with one another, and inputs the voltage signals V1-VM from the selected CDS device 50 into the A/D converter 52 serially. Note that an amplifier can be connected between the multiplexer 51 and the A/D converter 52.

A memory 54 is incorporated in the electronic cassette 13. The A/D converter 52 converts input voltage signals V1-VM of one array in an analog form into digital values, which are output to the memory 54. The digital values of the array are written to the memory 54 in association with coordinates of the pixels 41 by way of image data of the one array of the radiation image. Thus, the readout of the one array is terminated.

In case the multiplexer 51 reads out voltage signals V1-VM of one array from the integration amplifier 49, the controller 48 outputs a reset pulse RST to the integration amplifier 49, to turn on the reset switch 49c. Signal charge of one array stored in the capacitor 49b is discharged for the reset. After the pixel reset, the reset switch 49c is turned off again to hold one of the sample-hold circuits in the CDS devices 50 upon lapse of a predetermined time, to sample a kTC noise component of the integration amplifier 49. Then a gate pulse of a succeeding array is output by the gate driver 46, to start readout of signal charge of the pixels 41 of the succeeding array. Furthermore, the gate pulse is output to hold signal charge of the pixels 41 of the succeeding array by a second one of the sample-hold circuits in the CDS devices 50 upon lapse of the predetermined time. Those steps are successively repeated to read out the signal charge of the pixels 41 of all the arrays.

In case the readout of all the arrays is completed, the image data of one radiation image is written to the memory 54. The image data is read out from the memory 54, and processed for image processing of various functions by the controller 48. There is a communication interface 55 through which the image data is output to the console structure 14. Thus, the radiation image of the body is detected.

The communication interface 55 is connected with the console structure 14 in a wired or wireless manner, to send and receive information with the console structure 14. The communication interface 55 inputs information from the console structure 14 to the controller 48, the information including the imaging condition, a size of the radiation field and the special threshold for a pass-through area, the imaging condition having the stop threshold. The controller 48 supplies the AEC device 57 with information of the stop threshold. A field setting unit 56 or exposure field adjuster for an exposure field (receiving field) is supplied by the controller 48 with information of the radiation field and the special threshold.

In the pixel reset, dark current charge from the pixel 41 flows into the capacitor 49b of the integration amplifier 49 through the signal line 45 while the thin film transistor 43 is turned on. There is no readout of charge stored in the capacitor 49b with the multiplexer 51 in contrast with the readout operation. A reset pulse RST is output by the controller 48 in synchronism with the gate pulse G1-GN to turn on the reset switch 49c. Charge stored in the capacitor 49b is discharged to reset the integration amplifier 49.

The controller 48 includes various circuits (not shown) for image processing of various functions to image data of radiation images stored in the memory 54, for example, offset correction, sensitivity correction, defect correction and the like. The offset correction circuit subtracts an offset correction image from a radiation image per the unit of pixels, the offset correction image being obtained from the sensor panel 30 without irradiation of X-rays. The offset correction circuit eliminates constant pattern noise due to imaging environment or specificity of the signal processor 47. The sensitivity correction circuit is referred to also as a gain correction circuit, and corrects irregularity in the sensitivity of the photoconductors 42 of the pixels 41 and irregularity of an output characteristic of the signal processor 47. The defect correction circuit receives defective pixel information created at the time of shipment or periodical maintenance, and linearly interpolates pixel values of defective pixels by use of pixel values of normal pixels disposed around the defective pixels. Also, the defective correction circuit also interpolates the pixel values of the pixels 41 of arrays where monitoring pixels 41b or detection pixels are disposed. Note that the various image processing circuits can be incorporated in the console structure 14 to perform the image processing in the console structure 14.

The pixels 41 include active pixels 41a or normal pixels, and the monitoring pixels 41b. The active pixels 41a are used for generating a radiation image. The monitoring pixels 41b are dose sensors for detecting a dose of X-rays incident upon the active pixel area 40. Positions of the monitoring pixels 41b are predetermined and recognizable at the time of manufacturing the sensor panel 30. A non-volatile memory (not shown) in the sensor panel 30 stores coordinates of the positions of all the monitoring pixels 41b. In the drawing, the monitoring pixels 41b are hatched distinctly from the active pixels 41a.

Figure 6:
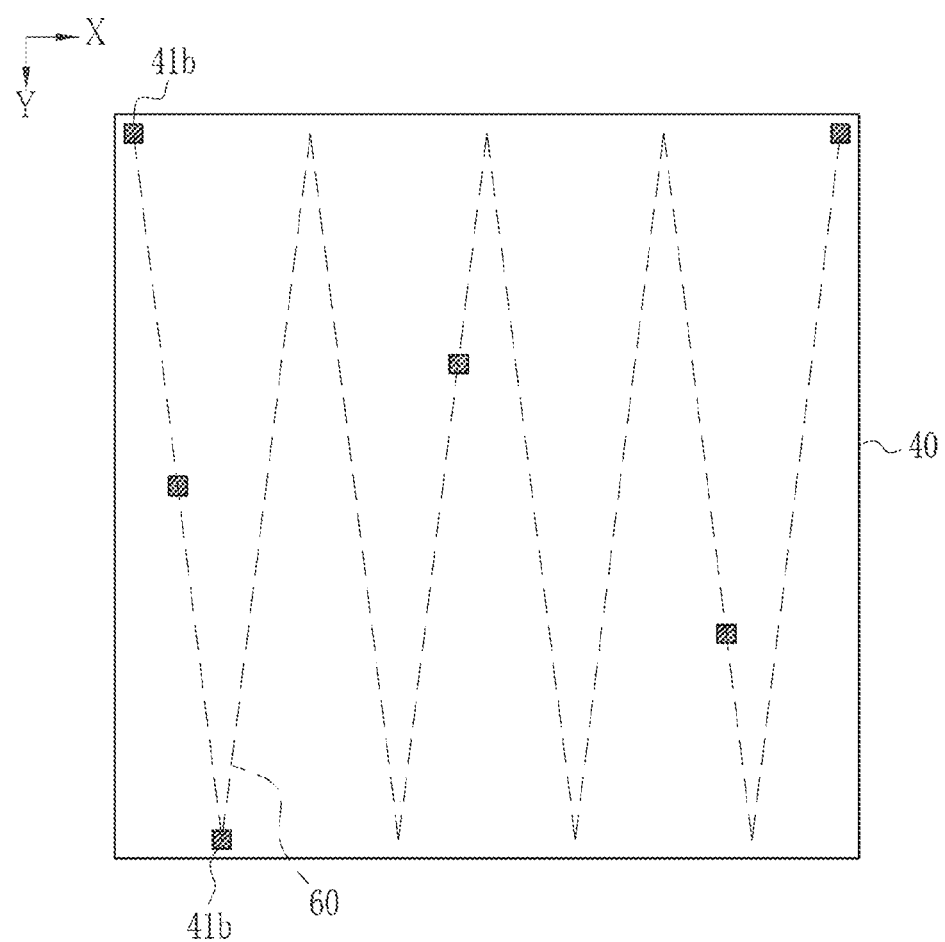
FIG. 6 is an explanatory view illustrating arrangement of monitoring pixels.

In FIG. 6, the monitoring pixels 41b are arranged along a reference line 60 or locus of the dotted line, which is in a wave shape and symmetric horizontally with reference to the center of the active pixel area 40. For each one of the arrays of the pixels 41 to which the same signal line 45 is connected, one of the monitoring pixels 41b is disposed. The monitoring pixels 41b are so disposed that two or three arrays without having the monitoring pixels 41b are arranged between arrays having the monitoring pixels 41b.

The monitoring pixels 41b are constructed in the same manner as the active pixels 41a in relation to a principal structure of the photoconductors 42 and the like. The monitoring pixels 41b can be manufactured in the same process as the active pixels 41a. In the monitoring pixels 41b, the source and drain in the thin film transistors 43 are short-circuited. Charge generated by the photoconductors 42 of the monitoring pixels 41b flows out to the signal line 45 irrespective of turn-on and turn-off of the thin film transistors 43, so as to read out a voltage signal according to the charge even while the thin film transistors 43 in the active pixels 41a are turned off in the same array to store the signal charge.

Charge generated by the photoconductors 42 of the monitoring pixels 41b is drawn into the capacitor 49b of the integration amplifier 49 through the signal line 45. The charge generated by the monitoring pixels 41b and stored in the integration amplifier 49 is output to the A/D converter 52, which converts the charge into a digital voltage signal, namely a dose signal. The dose signal is output to the memory 54. The dose signal is written to the memory 54 in association with coordinate information of the monitoring pixels 41b of the active pixel area 40. The sensor panel 30 performs the dose monitoring repeatedly in plural events at the same predetermined sampling period as the readout. The dose signal from the monitoring pixels 41b is written to the memory 54 in one event of sampling. The number of the monitoring pixels 41b is smaller than that of the active pixels 41a, but the monitoring pixels 41b are arranged in a discrete manner in the active pixel area 40. Regarding a dose signal from the monitoring pixels 41b as a pixel value makes it possible to utilize a dose signal in the memory 54 as information of a radiation image with a low resolution.

An allowance signal is output by a signal interface 58 for irradiation as a response to the request signal from the source driver 11. The sensor panel 30 starts the dose detection upon outputting the allowance signal from the signal interface 58. Note that a sampling period of the dose signal is defined as a period from starting integration of charge generated by the photoconductors 42 in the monitoring pixels 41b with the capacitor 49b of the integration amplifier 49 to converting the integrated charge into a voltage signal for outputting to the CDS device 50, in short, the period of integration of the integration amplifier 49.

The field setting unit 56 and the AEC device 57 are controlled by the controller 48 for operation. The field setting unit 56 and the AEC device 57 read out the dose signal from the memory 54 after sampling at a predetermined sampling period, to perform setting of an exposure field and perform the AEC according to the dose signal.

According to the dose signal of the monitoring pixels 41b read out from the memory 54, the field setting unit 56 sets an exposure field for monitoring a dose of X-rays for the AEC. For example, the exposure field is arranged and determined at a location of a ROI or region of the highest concern for the purpose of diagnosis. Let a chest of a body be imaged. Then a ROI is lungs of right and left sides for diagnosis of pulmonology.

To image the chest, the chest is oriented to face the active pixel area 40. However, other body parts of the body come to face the active pixel area 40, for example, portions of an arm and abdomen. The collimator of the X-ray source 10 sets a radiation field to cover a range of the body inclusive of the chest, arm and abdomen. The radiation field may be set to cover the entirety of the active pixel area 40, but is usually set to cover a smaller region than the active pixel area 40 in order to prevent unwanted exposure to radiation. Then a non-radiation field without irradiation is created around the radiation field inside the active pixel area 40. Also, a pass-through area (background area) is created in the radiation field where X-rays become incident directly without a portion of the body, for example, a space between the chest and arm.

At first, the field setting unit 56 specifies an exposure field in the active pixel area 40, and then specifies a body area except for a pass-through area, to recognize the exposure field finally from the inside of the specified body area according to image recognition. It is possible easily to recognize the exposure field finally with high precision, because of removing areas other than the exposure field in a stepwise manner.

Figure 7:
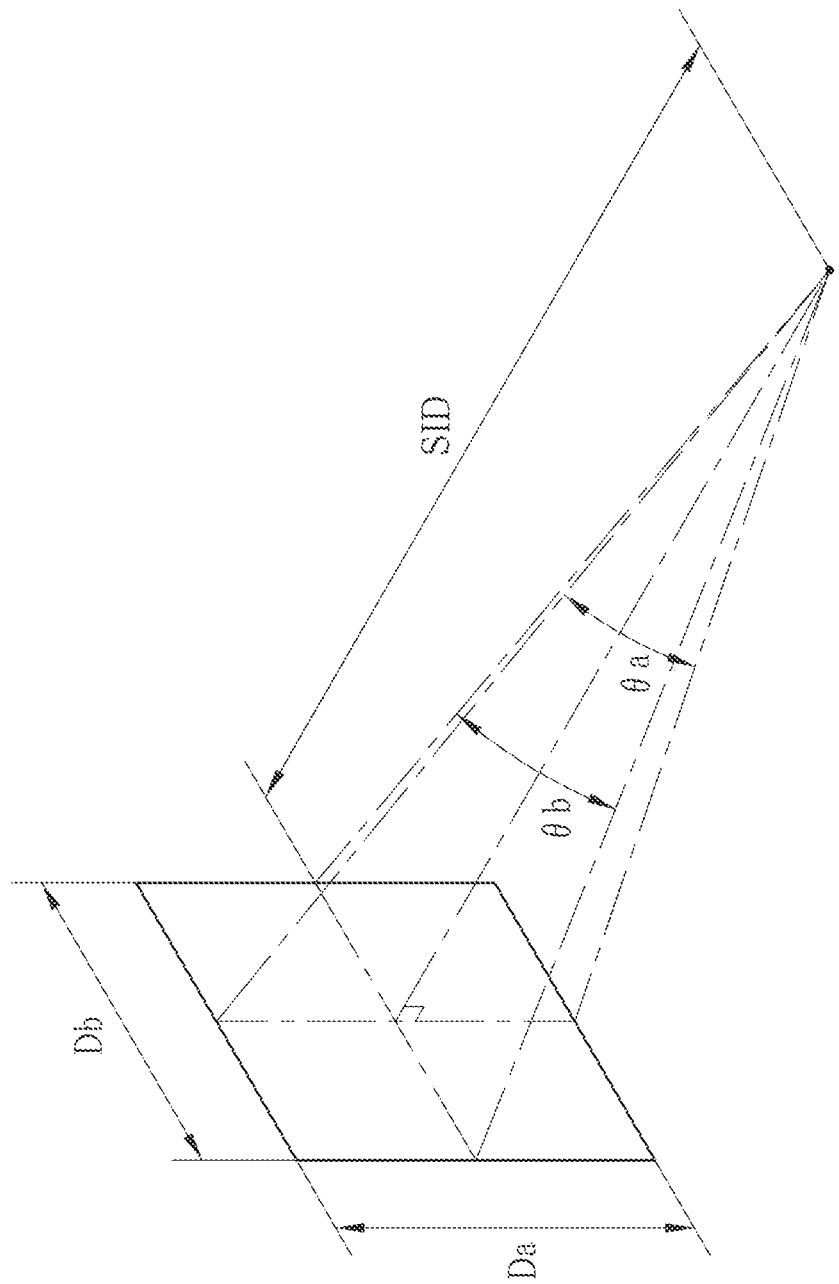
FIG. 7 is an explanatory view illustrating parameters for calculating a size of a radiation field.

A size of the radiation field can be obtained by calculation from the SID and the angular range of X-rays from the collimator. In FIG. 7, let θa and θb be angular ranges of X-rays of the vertical and horizontal directions. Sizes Da and Db of the radiation field in the vertical and horizontal directions are obtained by equations (1) and (2) as follows.

$$Da = 2 \cdot SID \cdot \tan(\theta a/2) \tag{1}$$

$$Db = 2 \cdot SID \cdot \tan(\theta b/2) \tag{2}$$

The console structure 14 substitutes the SID and the angular range of X-rays in both of the vertical and horizontal directions at the collimator for the items in the equations (1) and (2), and obtains the sizes Da and Db of the vertical and horizontal directions of the exposure field. The console structure 14 transmits the sizes Da and Db to the electronic cassette 13 by way of information of the radiation field.

The pass-through area is an area of direct entry of X-rays without passing through the body. An estimated dose of X-rays to reach the pass-through area can be estimated by calculation from the SID and imaging condition (tube voltage and tube current) irrespective of a body part of the body, for example, according to equations of the NDD method (numerical dose determination method). The console structure 14 determines the estimated value, and converts this into a threshold (hereinafter referred to as a special threshold) comparable with a dose signal output by the monitoring pixels 41b. The special threshold after the conversion is sent by the console structure 14 to the electronic cassette 13. The field setting unit 56 compares the dose signal from the monitoring pixels 41b with the special threshold, specifies the pass-through area, so that an area except for the specified pass-through area is designated as a body area.

Figure 8:
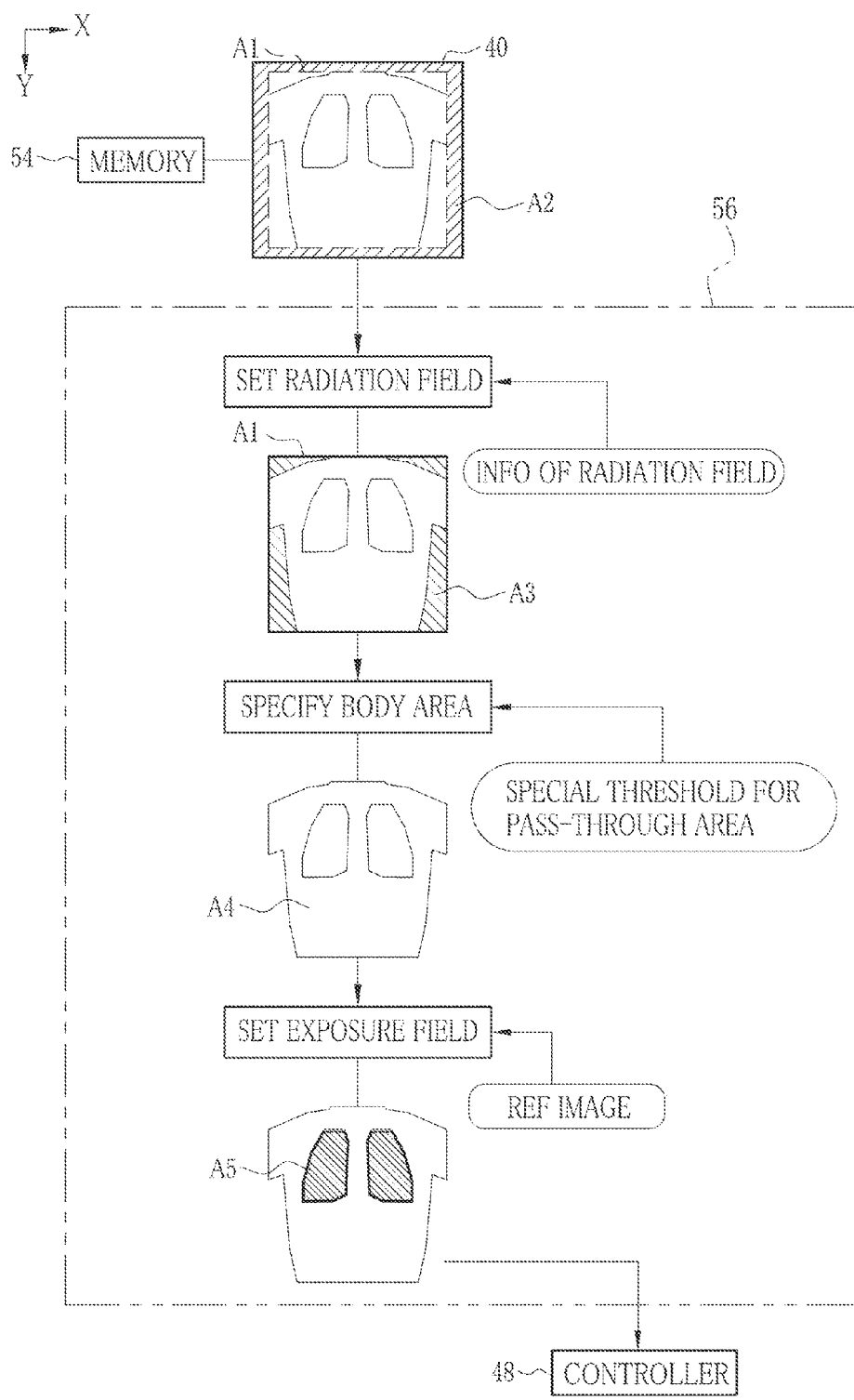
FIG. 8 is an explanatory view illustrating a field setting unit.

In FIG. 8 illustrating the function of the field setting unit 56 precisely, the field setting unit 56 specifies a radiation field A1 inside the active pixel area 40 corresponding to the sizes Da and Db of the radiation field output by the console structure 14. The field setting unit 56 selectively retrieves dose signals of the monitoring pixels 41b disposed in the radiation field A1 among the dose signals stored in the memory 54. Thus, dose signals of the monitoring pixels 41b disposed in the non-radiation field A2 are eliminated from the candidate signals of the exposure field.

Also, a radiation field can be specified by predetermining a threshold for the radiation field and by comparing the dose signal with the threshold. In a non-radiation field, a dose signal is approximately equal to zero. In view of this, the threshold is predetermined as small as zero. Assuming that the dose signal of an area is equal to or smaller than the threshold, then it is judged that the area is a non-radiation field. It is judged that a remaining area other than the non-radiation field is a radiation field.

Then the field setting unit 56 compares the dose signal of the monitoring pixels 41b positioned inside the radiation field A1 with a special threshold for specifying a pass-through area (background area) provided by the console structure 14, evaluates a result of the comparison, and eliminates the dose signal of the monitoring pixels 41b positioned inside the pass-through area A3 from candidates of an exposure field. In short, the dose signal of the monitoring pixels 41b disposed in the body area A4 receiving X-rays from the body is selectively retrieved.

Finally, the field setting unit 56 specifies the exposure field A5 from the previously specified body area A4 by use of the well-known image recognition in a shape exactly according to the shape of the ROI. For example, a radiation image as a reference is predetermined, to specify the exposure field A5 by use of pattern recognition of the specified body area A4 and reference image. For imaging the chest, right and left lungs as a ROI is specified as the exposure field A5. The position and size of an area opposed to the right and left lungs within the active pixel area 40 can be estimated. However, specificity occurs in the position and size of the lungs according to difference in the body of the patient. Also, the position and size of the body differ between an adult and child or between male and female bodies, so that a difference occurs in the position and size of the lungs. Furthermore, specificity occurs between male adults in relation to a height, body width and the like. Should an exposure field be set with reference to a position and size of lungs of one reference image, a body part other than the lungs is likely to enter the exposure field. Such a problem can occur because lungs of a child are smaller than those of an adult. Failure is likely to occur in properly detecting a dose suitable for the lungs. In view of this problem, it is preferable to prepare a plurality of reference images, selectively to use one reference image among those with highest degree of matching in the pattern recognition. Note that a reference image can be selected according to case information of a patient, such as an age, sex, height and the like, in compliance with specifics of the body of the patient.

Figure 9:
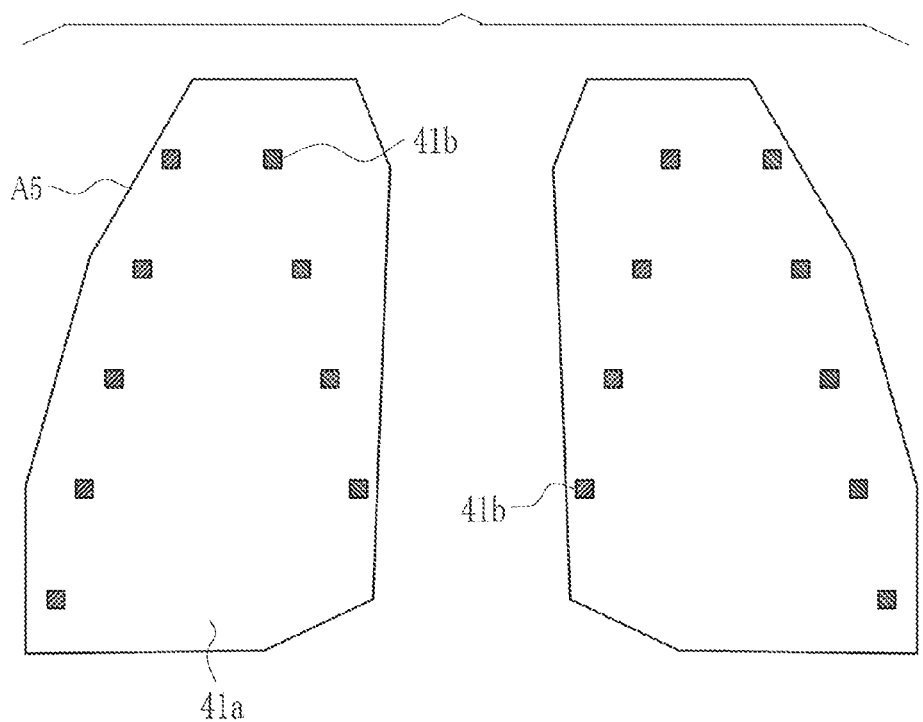
FIG. 9 is an explanatory view illustrating monitoring pixels arranged in an exposure field.

As the monitoring pixels 41b are arranged in the active pixel area 40 discretely as illustrated in FIG. 6, plural monitoring pixels 41b are arranged in the specified exposure field A5. See FIG. 9. The field setting unit 56 outputs field information of the specified exposure field to the controller 48. The field information is expressed by X and Y coordinates of the active pixels 41a and the monitoring pixels 41b disposed in the specified exposure field. The X and Y coordinates correspond to positions of the pixels 41 within the active pixel area 40 inclusive of the monitoring pixels 41b. For example, let the pixels 41 be arranged in a form of 2,000×2,000 of a matrix. An upper left corner pixel among the pixels 41 (the monitoring pixels 41b) is (1, 1). An upper right corner pixel among the pixels 41 is (1, 1999). The controller 48 outputs the field information to the AEC device 57. The controller 48 transmits the radiation image and the field information to the console structure 14 through the communication interface 55 in an associated manner.

In FIG. 8, dose signals of the monitoring pixels 41b in portions of the non-radiation field A2 of upper and lower ends and right and left ends of the active pixel area 40 are eliminated. Then dose signals of the monitoring pixels 41b of the pass-through area A3 over shoulders and between arms and body sides are eliminated. Finally, the right and left lungs as the exposure field A5 within the body area A1 are specified.

For time periods of specifying an exposure field in the field setting unit 56, it is possible to use a time period of an increase in the dose immediately after starting irradiation of X-rays, or to use a time period after stabilizing operation of the X-ray source 10 with a stable level of the dose according to the predetermined tube current. Although influence of noise may occur upon setting an exposure field during the period of the increase in the dose because of a relatively small value of the dose signal, it is possible to perform transition to the AEC smoothly, as the setting of the exposure field can be completed at the same time as starting irradiation of X-rays. While the time period after stabilizing operation of the X-ray source 10 is used for specifying an exposure field in the field setting unit 56, the dose signal obtained by the previous sampling is stored temporarily, and compared with the newly obtained dose signal. It is judged that the dose has become equal to the predetermined level in case the newly obtained dose signal becomes equal to the previous dose signal, so that setting of an exposure field is started. Consequently, a good S/N ratio can be obtained by a stabilized output of the dose signal in spite of considerable waiting time for a change of the dose signal, so that reliability in a result of setting an exposure field can be high.

The AEC device 57 measures a cumulative dose of X-rays to the exposure field by successively adding up dose signals from the memory 54 per coordinates after sampling of plural events. Specifically, the AEC device 57 calculates a representative value (average, maximum, mode value, total and the like) of the dose signals from the monitoring pixels 41b disposed in the exposure field set by the field setting unit 56. The representative value is accumulated to obtain the cumulative dose. For the purpose of precision, the dose signal read out from the memory 54 to the field setting unit 56 is also accumulated for setting the exposure field.

Figure 10:
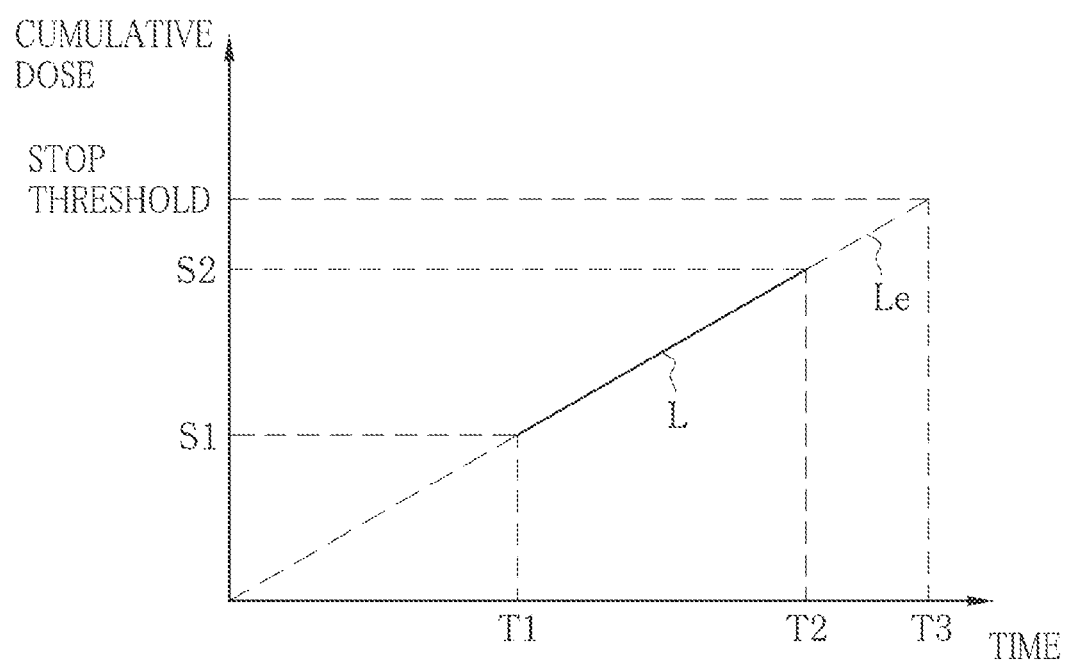
FIG. 10 is a graph illustrating estimation of a time point of reach of a cumulative dose to a target dose.

The AEC device 57 measures cumulative doses of the exposure field at two distinct time points, and determines an estimated time points of a reach of the cumulative dose to a target dose according to linear extrapolation according to the cumulative doses of the two time points. See FIG. 10. Specifically, a cumulative dose S1 of the exposure field is measured at a time point T1 upon a lapse of a predetermined time after setting the exposure field in the field setting unit 56. Also, a cumulative dose S2 of the exposure field is measured at a time point T2 upon a lapse of a predetermined time after the time point T1. A time point T3 of estimated reach of the cumulative dose to the target dose is obtained as a point of intersection between an extension line Le of a straight line L from a point of the cumulative dose S1 and time point T1 to a point of the cumulative dose S2 and time point T2 and a line of a stop threshold defined by conversion of the target dose. At the time point T3 after the lapse of time, the AEC device 57 outputs a stop signal to the controller 48, because it is judged that the cumulative dose of X-rays has become equal to the target dose.

The signal interface 25 of the source driver 11 is connected to the signal interface 58 in a wired or wireless manner. The signal interface 58 sends and receives a sync signal for sync control with the source driver 11. Examples of the sync signals include a request signal from the source driver 11 for starting irradiation, and an allowance signal to the source driver 11 in response to the request signal. Furthermore, a stop signal output by the AEC device 57 is received by the controller 48, which transmits the stop signal to the source driver 11.

Figure 11:
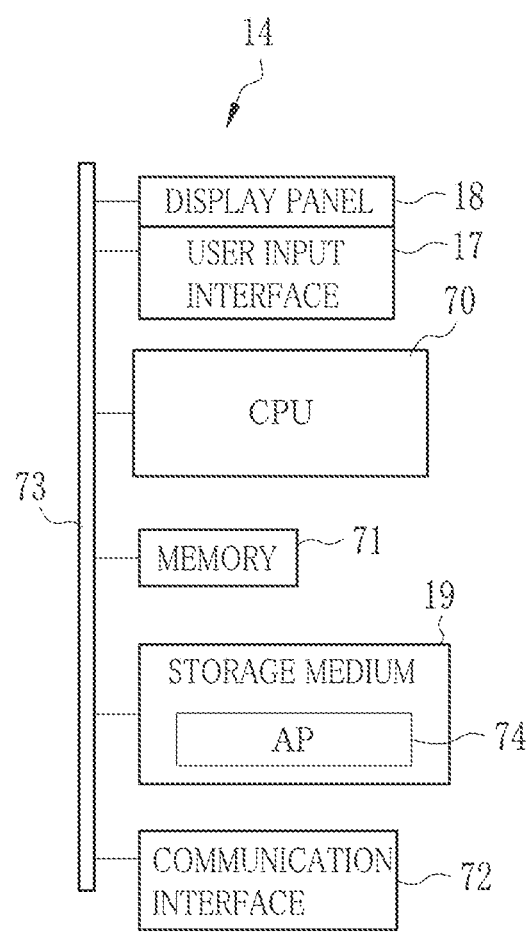
FIG. 11 is a block diagram illustrating a console structure.

In FIG. 11, a computer constituting the console structure 14 includes a CPU 70 (in a radiation image processing device), a memory 71 and a communication interface 72 in addition to the user input interface 17, the display panel 18 and the storage medium 19. There is a data bus 73 for interconnecting those elements.

Application programs 74 (AP) and the control programs are stored in the storage medium 19. The application programs 74 are run for the console structure 14 to perform various tasks in relation to X-ray imaging, including display processing of radiation images and information of a medical request, image processing of radiation images, setting of an imaging condition.

The memory 71 is a working memory with which the CPU 70 performs tasks. The control program stored in the storage medium 19 is loaded to the memory 71 by the CPU 70, to control the various circuit devices in the computer by performing the tasks according to the control program. The communication interface 72 is a network interface for wired or wireless connection with external apparatuses, such as the RIS, the HIS, an image server, the electronic cassette 13 and the like.

In FIG. 12, the CPU 70 of the console structure 14 is caused to have various circuit devices by running the application programs 74, inclusive of a matching unit 80 or position processor, a masking unit 81 or mask processor, a user interface controller 82 or input/output controller or display processor, and an information controller 83 or information reader.

The matching unit 80 and the masking unit 81 process radiation images from the electronic cassette 13 for image processing of various functions including position matching and masking, which will be described later. The user interface controller 82 reads out screen view data from the storage medium 19 according to inputs of the user input interface 17, and outputs information of various screens to the display panel 18 according to the screen view data. The user interface controller 82 receives an input signal from the user input interface 17 by use of the GUI (Graphical User Interface) on the display screen. Examples of the input signal are a search query of searching a radiation image to be displayed on the display panel 18, a command signal for driving the matching unit 80 for position matching, and the like. Examples of the search query include a keyword (describer) for designating a particular radiation image, such as a patient's name, patient ID, imaging date, object of interest, and the like.

The information controller 83 operates as an image acquisition unit in addition to an information reader. The information controller 83 receives field information and a radiation image from the electronic cassette 13 through the communication interface 72, and writes those to the storage medium 19. The information controller 83 functions also as a searcher, which is responsive to a search query of a radiation image from the user input interface 17, and searches and acquires the field information and the radiation image from the storage medium 19 according to the search query. The information controller 83 sets the acquired radiation image to the matching unit 80 or the user interface controller 82.

Figure 13A:
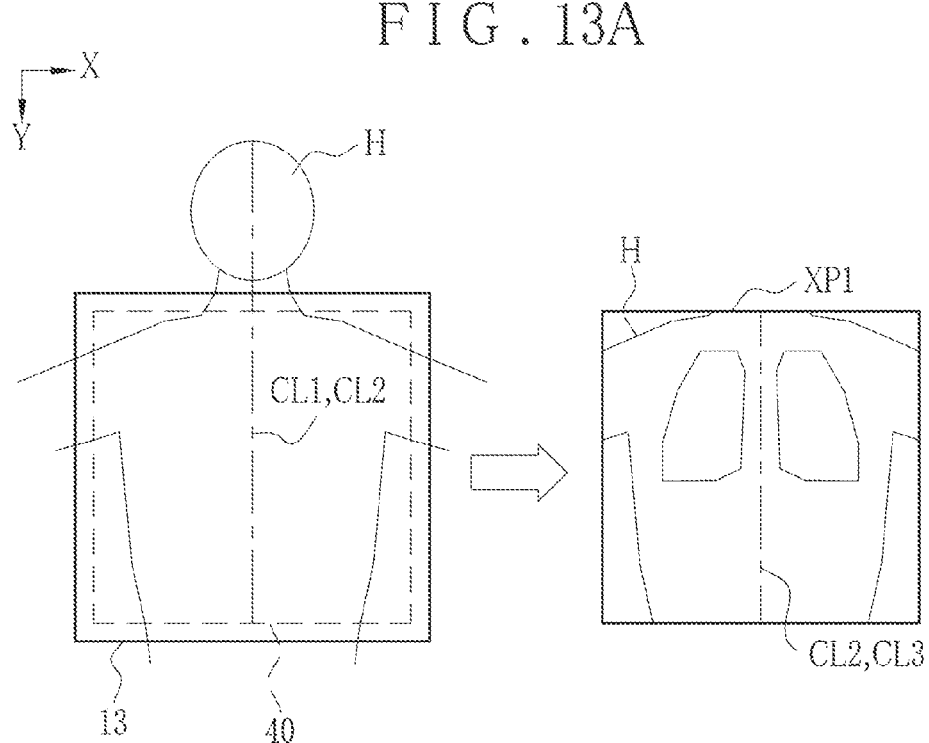
FIG. 13A is an explanatory view illustrating a relative position between an object and a position of the object arranged in a radiation image.
Figure 13B:
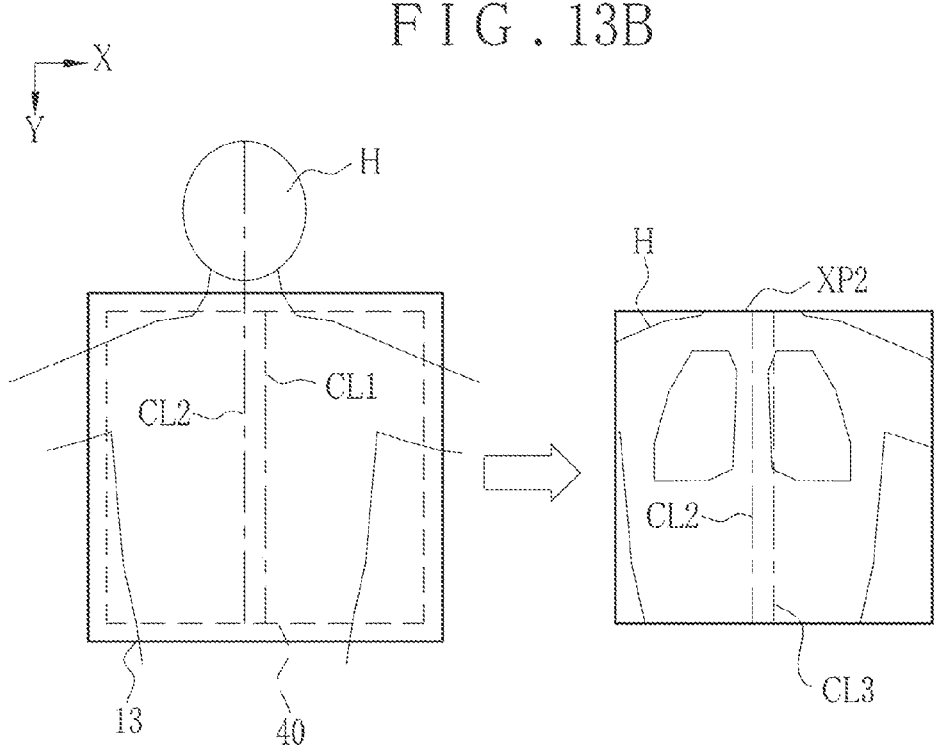
FIG. 13B is an explanatory view illustrating a relative position between an object and a position of the object arranged in a second radiation image.

For the matching unit 80, one object of interest of one body is imaged at a plurality of events with a time interval, to obtain plural radiation images. The matching unit 80 performs a task of position matching of a position of the body in the plural radiation images according to plural display images corresponding to the radiation images. In FIGS. 13A and 13B, a position of the body H arranged in the radiation images XP1 and XP2 is changed by a change in the position of the body H positioned relative to the active pixel area 40. In FIG. 13A, the center line CL2 of the body is matched to the center line CL1 of the active pixel area 40. The body H in the radiation image XP1 is located at its center. Specifically, the center line CL2 of the body H is substantially matched to the center line CL3 of the radiation image XP1. In contrast, the body H in FIG. 13B is positioned on a left side in the X direction. The center line CL2 of the body H is offset from the center line CL1 of the active pixel area 40 on the left side in the X direction. The body H arranged in the radiation image XP2 is also offset from the center line CL3 of the radiation image XP2 on the left side.

The user interface controller 82 produces a display image according to a radiation image to be displayed on the display panel 18. In general, the user interface controller 82 performs display processing of an image in an area of a video memory, and outputs the processed image to the display panel 18 as a video signal. Various parameters of the processed image in the video memory are determined according to specifics of the display panel 18 or the application programs 74 for display processing, or according to user's preference, including a resolution, number of pixels, display size and the like. The display image is for the purpose of displaying the radiation images on the display panel 18 as an output of display processing from the video memory, and formed by correction of the radiation image in relation to the resolution, number of pixels, display size and the like according to the specifics of the display panel 18 or the application programs 74 for display processing. An example of the video memory is a partial area included in the memory 71. Note that a video memory can be a separate memory distinct from the memory 71.

In FIGS. 14A and 14B, an outline of display is illustrated, inclusive of steps of generating display images DXP1 and DXP2 from radiation images XP1 and XP2, and displaying the generated display images DXP1 and DXP2 in a screen view 18a of the display panel 18. The display processing is performed by the user interface controller 82. The display frame F is set in the video memory, and used for setting arrangement positions and display sizes of the display images DXP1 and DXP2 in the screen view 18a. Note that the display frame F on the video memory corresponds to a display frame disposed in the screen view 18a. The identical reference sign F is used commonly for the clarification as illustrated in FIGS. 14A and 14B.

To produce a display image from a radiation image, an area for use in the display image is trimmed from the radiation image in a size suitable for the display frame F. In FIGS. 14A and 14B, let an aspect ratio of the display frame F be equal to that of the radiation images XP1 and XP2. Thus, the entire areas of the radiation images XP1 and XP2 are trimmed or adapted as the display images DXP1 and DXP2. In case there is a difference in the aspect ratio, partial areas of the radiation images XP1 and XP2 are trimmed as the display images DXP1 and DXP2. Should the size of trimming from the radiation image is larger than the display frame F, a surplus portion outside the display frame F does not appear on the screen view 18a.

In FIG. 14A, the entire area of the radiation image XP1 is arranged in the display frame F in the video memory in the display processing of the radiation image XP1. The arrangement is performed for matching the center line CL3 of the radiation image XP1 to the center line CL4 of the display frame F. The center line CL3 of the radiation image XP1 matches to the center line CL2 of the body H. The matching between the center line CL3 of the radiation image XP1 and the center line CL4 of the display frame F also causes matching to the center line CL2 of the body H. Thus, the display image DXP1 is displayed on the screen view 18a by setting the body H concentric with the center of the display frame F.

In FIG. 14B, display processing of the radiation image XP2 is illustrated. The entire area of the radiation image XP2 is arranged in the display frame F as the display image DXP2 in a manner similar to the radiation image XP1. In relation to the arrangement position, the center line CL3 of the radiation image XP2 matches to the center line CIA of the display frame F. However, the center line CL3 of the radiation image XP2 is not matched to the center line CL2 of the body H differently from the radiation image XP1. Even in case the center line CL3 of the radiation image XP2 is matched to the center line CL4 of the display frame F, the center line CL2 of the body H is not matched to the center line CL4 of the display frame F. A problem arises in that the display image DXP2 is displayed in such an off-center manner that the body H is eccentric from the display frame F.

Figure 15:
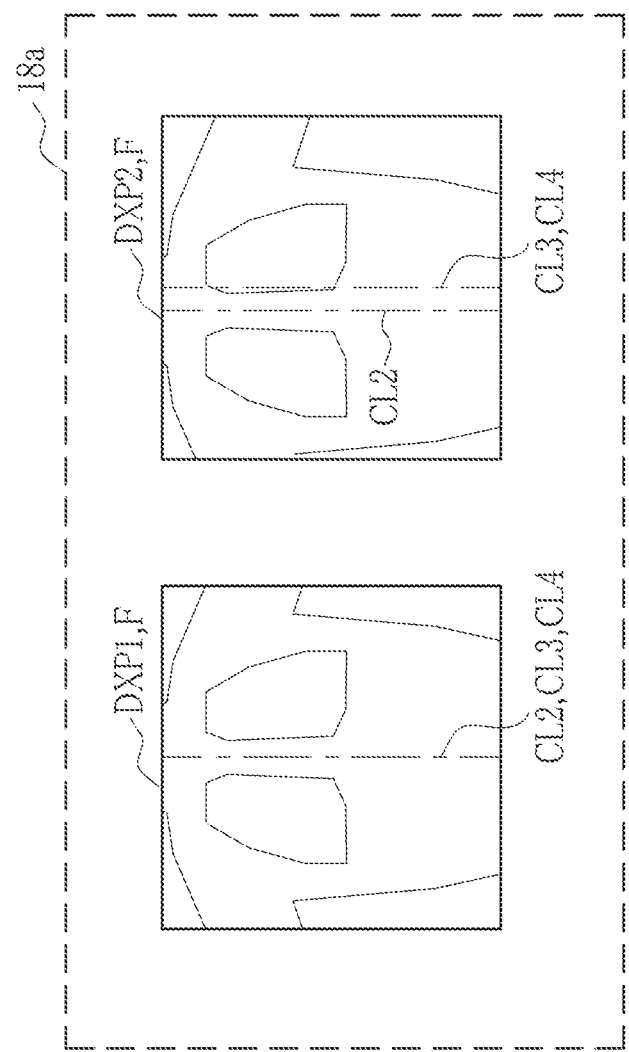
FIG. 15 is an explanatory view illustrating a radiation image without position matching.

In FIG. 15, two display frames F are arranged in the screen view 18a for interpretation of the radiation images XP1 and XP2. A display image DXP1 corresponding to the radiation image XP1 and a display image DXP2 corresponding to the radiation image XP2 are displayed in the display frames F. There occurs a difference in the position of the body H between the display images DXP1 and DXP2 in the display frames F. The difference is a problem in view of the purpose of the image interpretation. Thus, the matching unit 80 performs the position matching in order to eliminate the position offset.

The matching unit 80 selects one of the radiation images (for example, images XP1 and XP2) as a reference image. A position of an exposure field of another radiation image is matched to a position of an exposure field of the selected reference image. Thus, the position of the body within the display images (for example, display images DXP1 and DXP2) on the screen view 18a is matched. An example of the reference image is a radiation image obtained in a first event of imaging among plural radiation images. Designation of the radiation image of the first imaging can be recognized by referring to a calendar date of the imaging among auxiliary data of the radiation image. Note that an example of the reference image may be a radiation image obtained in a newest event of imaging. Furthermore, it is possible to display plural radiation images on the display panel 18 at the time of inputting a command signal for the position matching, and selectively to designate one of the radiation images as a reference image by manual operation of a user or operator. Also, it is possible to predetermine a reference point of positioning for each of body parts instead of selecting a reference image among the plural radiation images.

In case the radiation image obtained in the first event of imaging is used as the reference image, or in case the reference point is predetermined irrespective of the plural radiation images, manual specifying operation of an operator can be saved. Also, in case a reference image is designated manually by a user or operator, one of the radiation images with good positioning of the body is selected generally. Plural radiation images after the positioning can be easily viewed for diagnosis.

For interpretation of the radiation images XP1 and XP2 in comparison, the user interface controller 82 performs display processing for each of the radiation images XP1 and XP2. See FIG. 16. Description of the present embodiment is made herein in relation to the radiation image XP1 set as the reference image BP and the radiation image XP2 set as the object image OP to be positioned relative to the reference image BP. For the display processing of the radiation image XP1 as the reference image BP, the user interface controller 82 outputs the display frame F as illustrated in FIG. 14A, and generates the display image DXP1 to match the center line CL3 of the radiation image XP1 to the center line CL4 of the display frame F. For the display processing of the radiation image XP2 as an object image OP, the radiation image XP2 is processed for position matching by the matching unit 80 and processed for masking by the masking unit 81 in addition to outputting the display frame F, to generate the display image DXP2. The matching unit 80 operates for the position matching according to the field information I1 of the radiation image XP1 and the field information I2 of the radiation image XP2. The matching unit 80 receives the field information I1 and I2 from the information controller 83.

Figure 17:
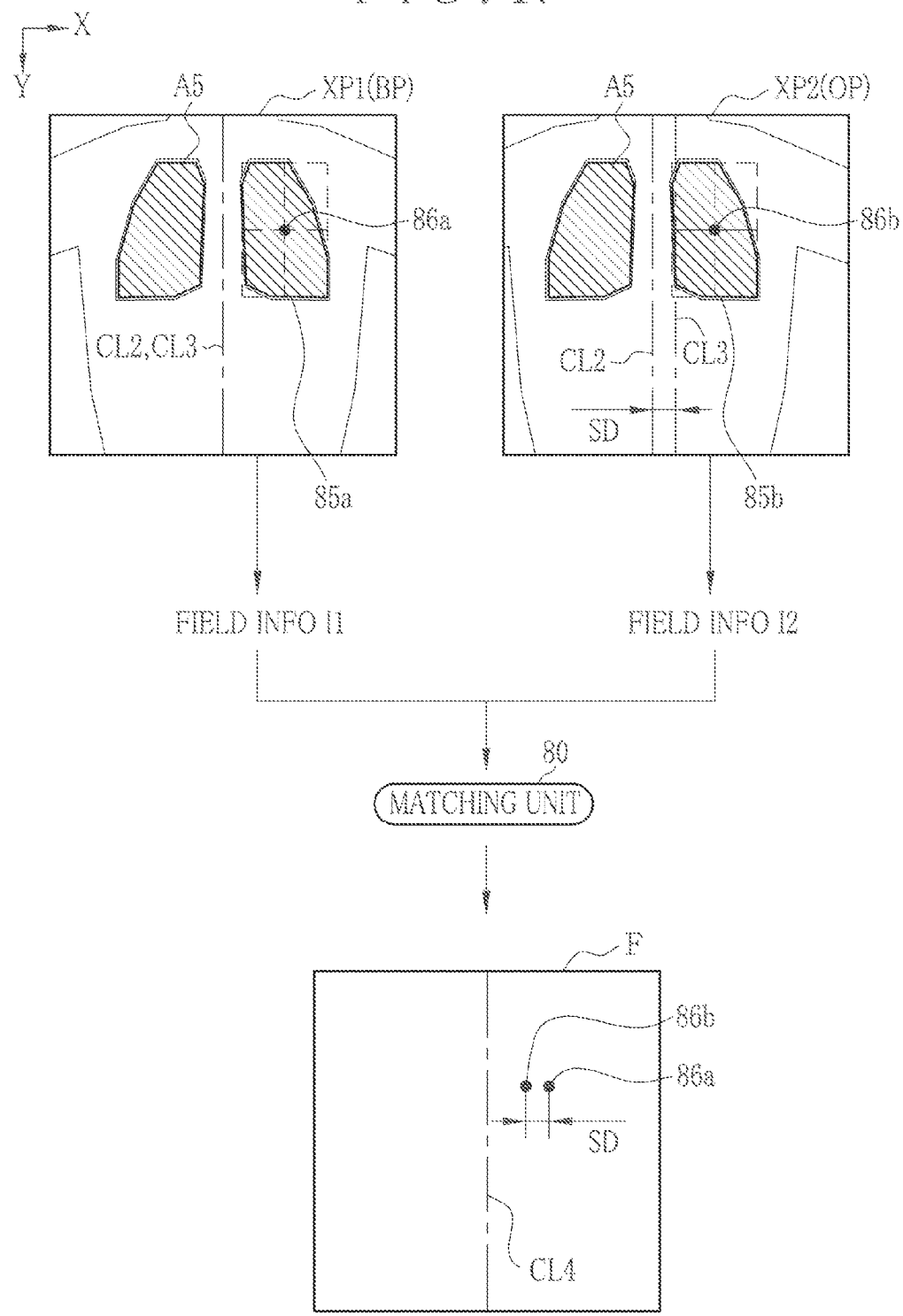
FIG. 17 is an explanatory view illustrating calculation of a position offset.

In FIG. 17, the matching unit 80 determines coordinates of quadrilateral frames 85 (85a and 85b) of the exposure field A5 of each of the radiation images XP1 and XP2, and their centers (86a and 86b) or reference points according to the field information I1 and I2. Each of the quadrilateral frames 85 is disposed around the exposure field A5 and tangential to the profile line of the exposure field A5. In the presence of the plural exposure fields A5 for the right and left lungs of the present embodiment, coordinates of the quadrilateral frames 85 and the centers 86 are calculated for only one of the exposure fields A5. In the drawing, coordinates of the quadrilateral frames 85 and the centers 86 for the left lung are determined.

The matching unit 80 calculates the position offset SD (including a direction of the offset) between the reference image BP and the object image OP in the display frames F according to the center 86a of the quadrilateral frame 85a of the reference image BP (radiation image XP1) and the center 86b of the quadrilateral frame 85b of the object image OP (radiation image XP2). The field information I1 and I2 is information in which the position of the body H in the radiation images XP1 and XP2 is considered. The position offset SD corresponds to a shift between the center line CL3 of the radiation image XP2 and the center line CL2 of the body H.

Changes in the size include an increase and decrease in the size. Assuming that the size of the display images DXP1 and DXP2 is smaller than that of the radiation images XP1 and XP2 with a decrease, then a position offset SD of the radiation image XP2 and a position offset SD of the display frame F are changed according to a ratio of the change in the size (ratio of the increase or decrease). In the present embodiment, description is made for an example of an unchanged size.

Figure 18:
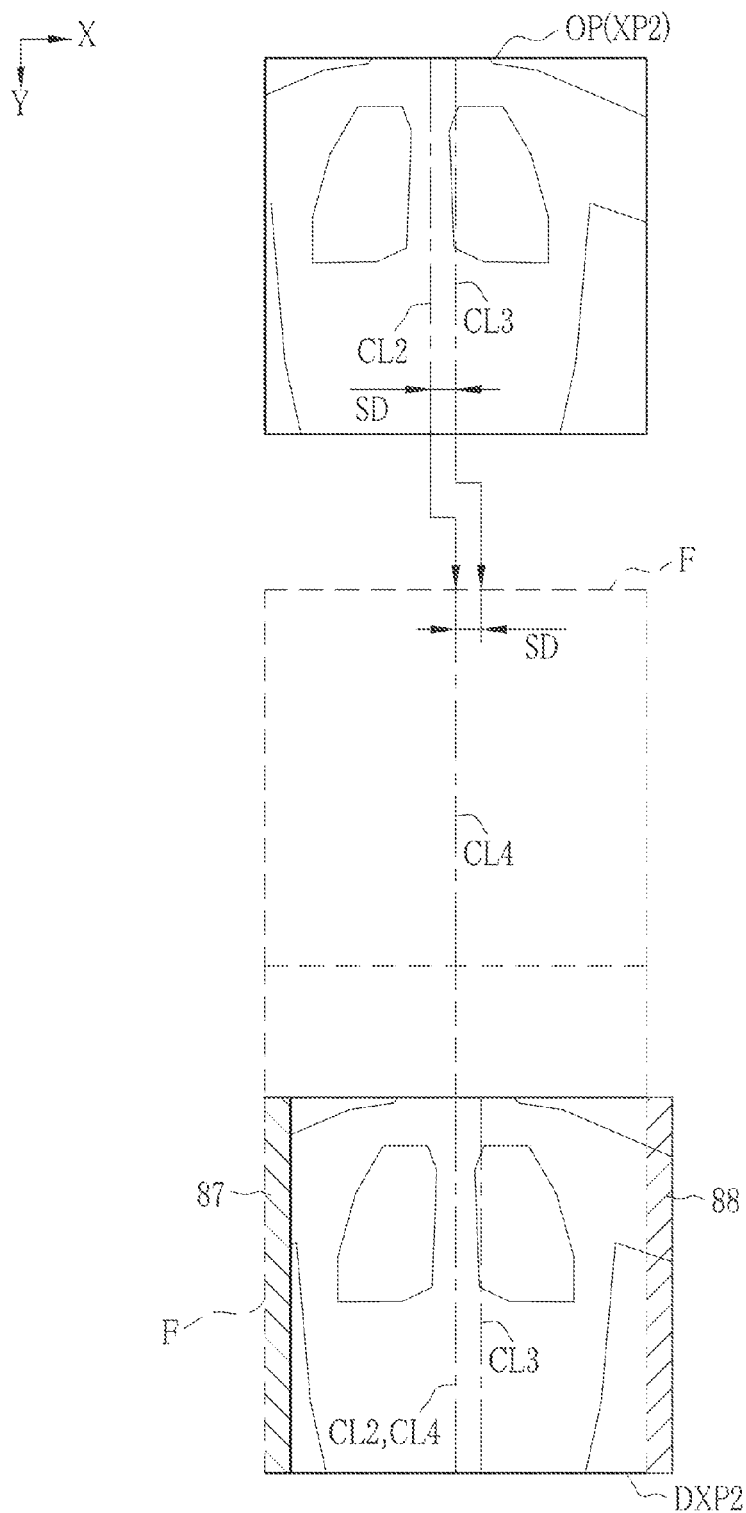
FIG. 18 is a plan illustrating position matching.

In FIG. 18, the matching unit 80 shifts the center line CL3 of the radiation image XP2 relative to the centerline CL4 of the display frame F by the position offset SD. In short, an arrangement position of the display image DXP2 in the display frame F is shifted by the position offset SD. The position offset SD is defined as a shift amount for the arrangement position relative to the display frame F. The center line CL2 of the body H differs between the radiation image XP2 as the object image OP and the radiation image XP1 as the reference image BP. However, the positioning matches the center line CL2 of the body H to the center line CL4 of the display frame F in the display image DXP2 in the same manner as the display image DXP1.

Thus, the body H in the display image DXP2 of the radiation image XP2 (object image OP) is disposed at the center similarly to the body H in the display image DXP1 of the radiation image XP1 (reference image BP). Thus, an offset between the position of the body H in the display image DXP1 and the position of the body H in the display image DXP2 can be removed.

In the embodiment, the body H in the reference image OP (radiation image XP2) is offset only in the X direction relative to the body H in the reference image BP (radiation image XP1). However, the position matching is performed also for images with an offset only in the Y direction and images with an offset in both of the X and Y directions, by obtaining the position offset SD according to the field information I1 and I2. For the images with an offset of the body H only in the Y direction, a position offset SD in the Y direction is obtained. For the images with an offset of the body H in both of the X and Y directions, a position offset SD after combining component vectors of offsets of the X and Y directions according to the field information I1 and I2 is obtained. Thus, the position offset of the body H in the display images is eliminated by the position matching according to the position offset SD.

Also, it is possible to obtain a gravity center of a specified exposure field and its coordinates according to a shape exactly corresponding to a ROI, to use the gravity center as a reference point of the position matching, in place of the coordinates of the centers 86 of the quadrilateral frames 85.

Figure 19:
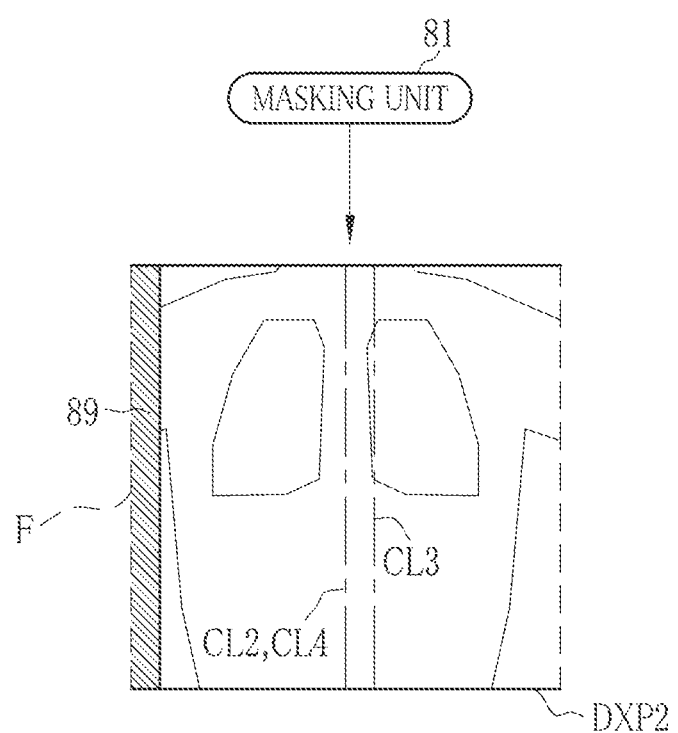
FIG. 19 is an explanatory view illustrating masking.

In FIG. 18, an arrangement position of the display image DXP2 is shifted by the position offset SD in the display frame F, where a blank portion 87 and a surplus portion 88 are created. The blank portion 87 is formed by lack of image information. The surplus portion 88 is a portion of the display image DXP2 projecting from the display frame F. In FIG. 19, the masking unit 81 processes the blank portion 87 in the masking, for example, blackening. A black image 89 is created to fill the blank portion 87. As the surplus portion 88 is not inside the display frame F, the surplus portion 88 does not appear in the display panel 18. Note that the masking can be performed with a color other than black, for example, gray, white or the like.

In case there are plural object images OP, the matching unit 80 and the masking unit 81 process the plural object images OP for the position matching and masking. The matching unit 80 and the masking unit 81 produce display images of the plural radiation images for the interpretation in comparison.

Assuming that a user wishes to store a display image after the position matching and masking, the CPU 70 writes the processed display image to the storage medium 19 in association with the corresponding radiation image. It is also possible to store information of the position offset SD in the position matching to the storage medium 19 in addition to the display image or in place of the same.

Figure 20:
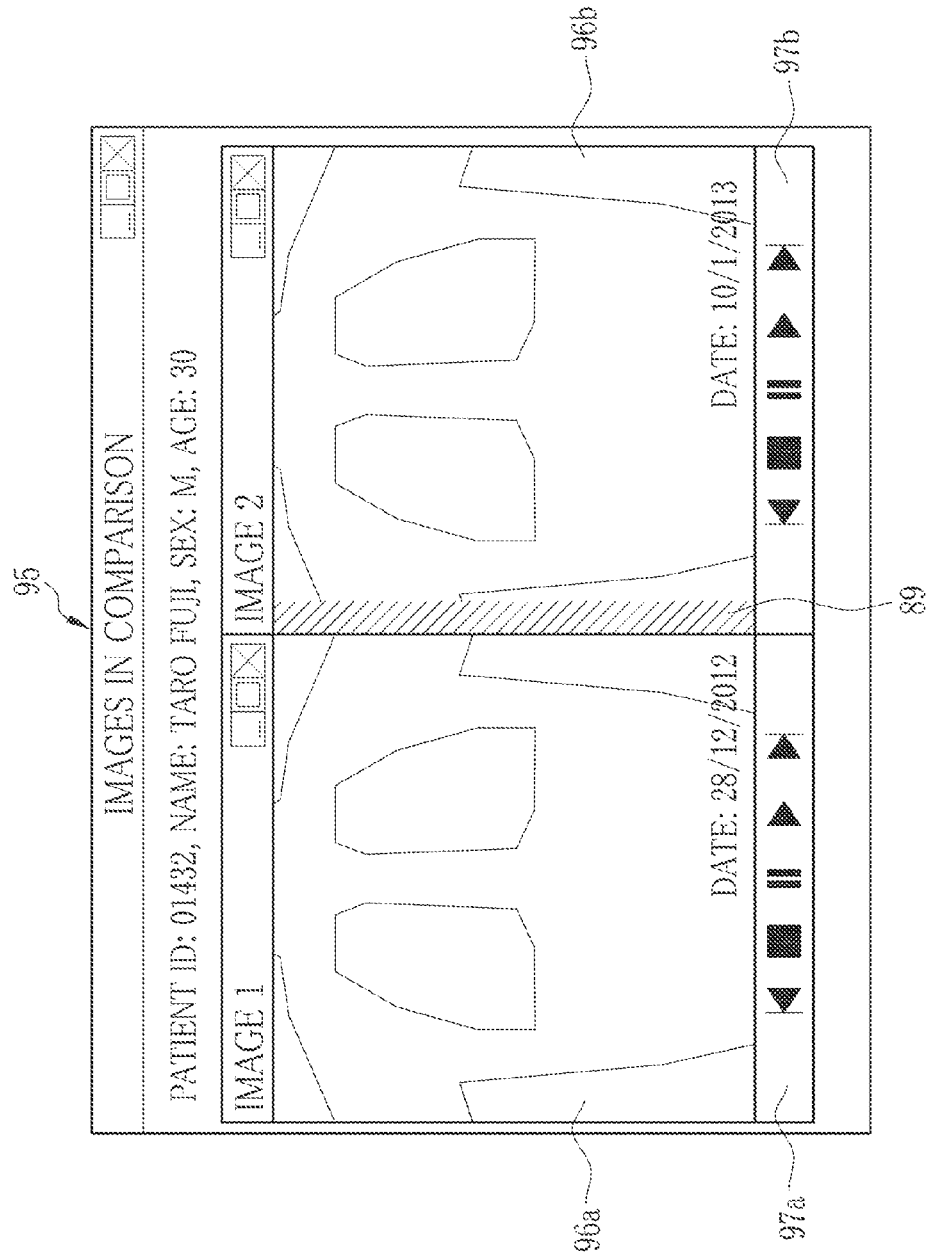
FIG. 20 is a plan illustrating a comparison window.

In FIG. 20, a comparison window 95 is displayed in the screen view 18a of the display panel 18 by the user interface controller 82 for the image interpretation in comparison. The display images DXP1 and DXP2 are displayed in the comparison window 95. Information of the object is displayed in the comparison window 95, inclusive of a patient ID, name and the like. Also, two sub windows 96a and 96b or view windows are arranged in the comparison window 95 in correspondence with the display frame F in the screen view 18a. The display images DXP1 and DXP2 (images 1 and 2) are displayed in the sub windows 96a and 96b in a horizontally arranged manner together with a calendar date of imaging. The position matching is performed for the display image DXP2 in the sub window 96b to eliminate offset of the body H. Also, a left edge of the display image DXP2 is provided with the black image 89 by the masking. A user or operator can view the display images DXP1 and DXP2 arranged in the comparison window 95.

Control bars 97a and 97b are disposed under the sub windows 96a and 96b. Assuming that there are two or more radiation images for image interpretation, the control bars 97a and 97b are operated to change over the display images in the sub windows 96a and 96b. It is possible to change over the display images automatically at a predetermined interval, to stop the automatic changeover in a temporary manner or the like, and to feed the display image from frame to frame forwards or backwards by one frame. The number of the images arranged in the display may not be two, but can be three or more. Furthermore, only one sub window can be used in place of using the plural sub windows for display images. The plural display images can be changed over one after another within the one sub window. Also, a plurality of display images may be displayed simultaneously in an overlapped manner. Various types of those display methods can be selected according to user's preference.

Figure 21:
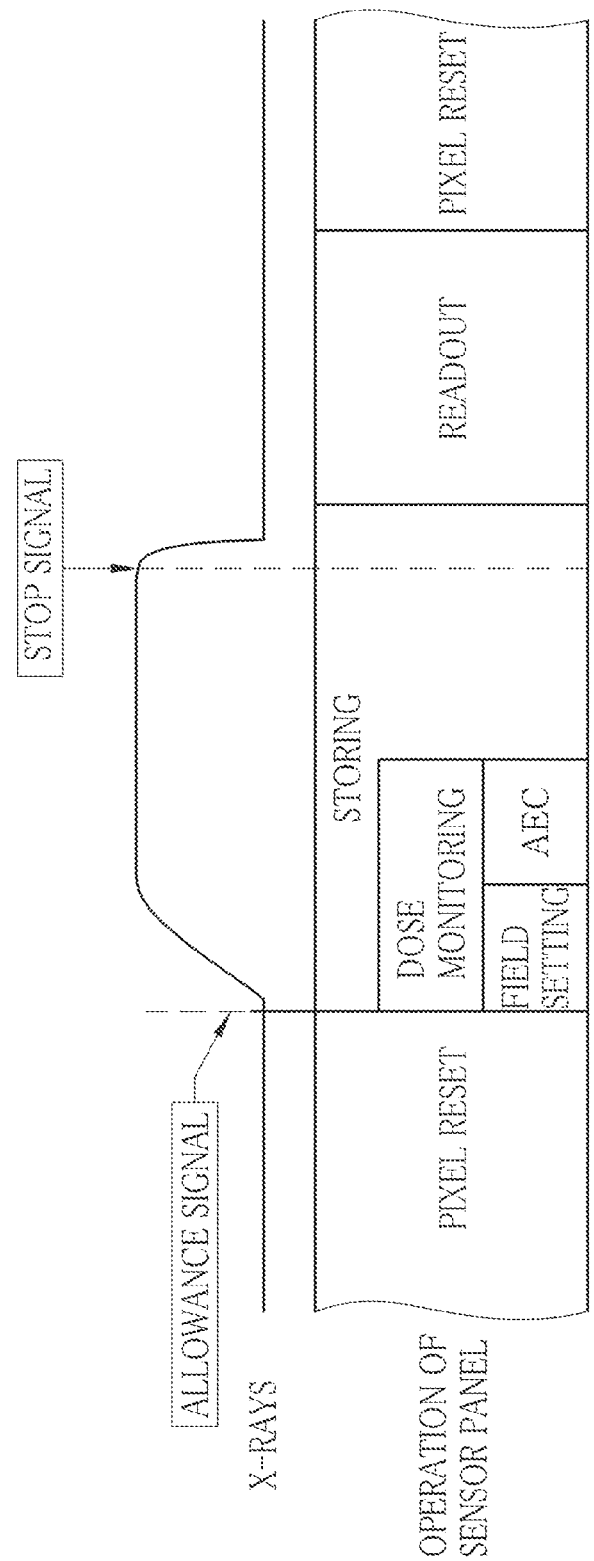
FIG. 21 is a timing chart illustrating operation of a sensor panel in X-ray imaging.
Figure 22:
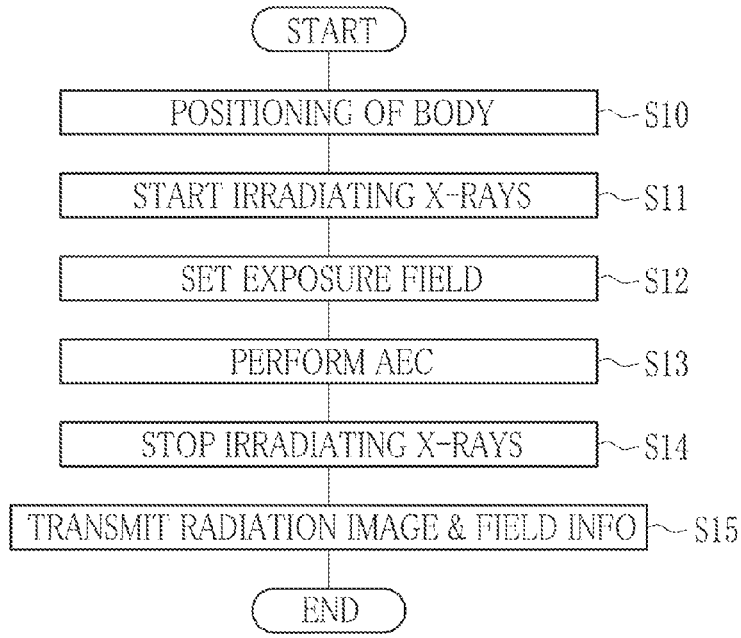
FIG. 22 is a flow chart illustrating the X-ray imaging.
Figure 23:
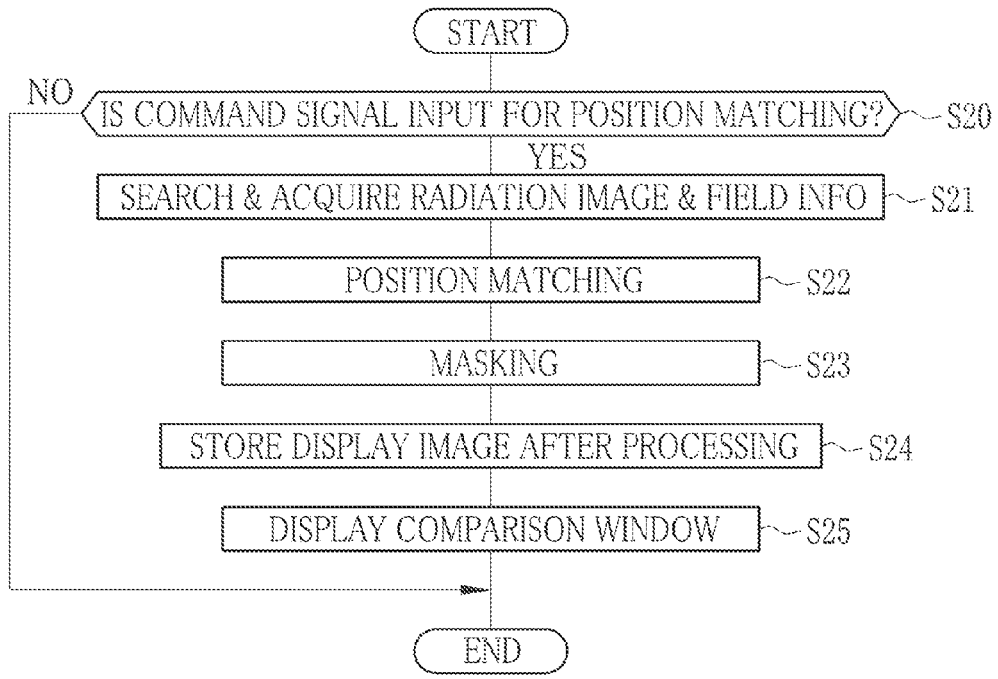
FIG. 23 is a flow chart illustrating operation of a console structure.

The operation of the above-described construction is described now by referring to FIGS. 21, 22 and 23. In FIG. 22, the body is set at either one of the floor stand 15 and the patient table 16 for X-ray imaging in the X-ray imaging system 2. A height, horizontal position and the like of the electronic cassette 13 are adjusted to position the body for imaging in the step S10. According to the position of the electronic cassette 13 and a size of the object of interest, a height and horizontal position of the X-ray source 10 and a size of the radiation field are adjusted. Then an imaging condition is set in the source driver 11 and the console structure 14. An angular range of X-rays and the SID are input to the console structure 14. Note that the step of inputting is omitted assuming that the angular range of X-rays and the SID have been already input.

In case the imaging is ready, the user or operator depresses the radiation switch 12 halfway. In response, the source driver 11 transmits a start signal for warmup to the high voltage source 21, to warm up the X-ray source 10. Also, the source driver 11 transmits a request signal for irradiation to the electronic cassette 13.

In FIG. 21, the sensor panel 30 in the electronic cassette 13 performs the pixel reset repeatedly before the X-ray imaging, and stands by for receiving a request signal for start. In case the sensor panel 30 receives the request signal from the source driver 11, the sensor panel 30 checks the status, and then transmits an allowance signal to the source driver 11. At the same time, the sensor panel 30 terminates the pixel reset, and starts the storing and the dose monitoring simultaneously.

Upon receiving an allowance signal from the sensor panel 30 and upon full depression of the radiation switch 12, the source driver 11 transmits a start signal to the high voltage source 21, for the X-ray source 10 to start irradiation of X-rays in the step S11. X-rays from the X-ray source 10 pass through the body and become incident upon the sensor panel 30.

In the sensor panel 30, the charge generated by the active pixels 41a is stored in the photoconductors 42. The charge generated by the monitoring pixels 41b is drawn to the capacitor 49b of the integration amplifier 49 from the signal line 45, as the thin film transistors 43 are short-circuited. The sensor panel 30 reads out the charge from the monitoring pixels 41b at a predetermined sampling period repeatedly. The dose signal obtained by the sampling is written to the memory 54, and read out from the memory 54 to the field setting unit 56 at each time of the sampling.

At first, the field setting unit 56 selectively retrieves dose signals of the monitoring pixels 41b positioned in the radiation field among dose signals stored in the memory 54 on the basis of information of a size of the radiation field from the console structure 14. Also, the field setting unit 56 selectively retrieves dose signals of the monitoring pixels 41b positioned in a body area by comparing the dose signals of the monitoring pixels 41b in the radiation field and the special threshold from the console structure 14 for the pass-through area. Finally, an exposure field (receiving field) is determined from the body area by use of the technique of the image recognition in the step S12. Note that the exposure field is specified in FIG. 21 in a period of an increase in the dose immediately after the start of irradiation of X-rays. However, it is possible to specify an exposure field after a level of the dose becomes stable at a predetermined value, as described above.

The AEC device 57 reads out the dose signal of the monitoring pixels 41b from the memory 54, the monitoring pixels 41b being positioned in the exposure field set by the field setting unit 56. The AEC device 57 calculates a cumulative dose of the exposure field. According to the cumulative doses S1 and S2 of the exposure field measured at two time points T1 and T2 with a time difference, the AEC device 57 calculates a time point T3 estimated for a reach of the cumulative dose to a target dose by the linear extrapolation, in the step S13. At the time T3 of the estimation, the AEC device 57 outputs a stop signal to the controller 48 for irradiation. The stop signal is transmitted to the source driver 11. Upon receiving the stop signal, the source driver 11 turns off the X-ray source 10 to stop irradiation of X-rays in the step S14.

In the sensor panel 30, the active pixels 41a perform the storing after transmission of the allowance signal. Upon lapse of a predetermined time after outputting a stop signal from the AEC device 57, the sensor panel 30 is changed over from the storing to the readout. Image data of one radiation image is output to the memory 54. After the readout, the sensor panel 30 is changed over to the pixel reset again. In the irradiation profile of X-rays, the dose after outputting the stop signal does not become zero abruptly but decreases gradually with a decay portion. In the present embodiment, the storing is changed over to the readout upon lapse of the predetermined time after generating the stop signal, in order to absorb the decay portion.

The various devices in the controller 48 for image processing perform image processing for the radiation image having been output to the memory 54 by the readout. The processed radiation image is transmitted to the console structure 14 together with associated field information in the step S15. Thus, one event of the X-ray imaging is completed. For observing a progress of the body of the patient, the object of interest in the body is imaged in a first event of the X-ray imaging before the treatment or surgical operation. In case three day, one week or one month elapses after the treatment, the same object of interest in the body H is imaged in a second event of the X-ray imaging.

In the console structure 14, the field information and the radiation image transmitted from the electronic cassette 13 is received by the communication interface 72 and written to the storage medium 19 by control of the information controller 83. Also, plural radiation images are stored to the storage medium 19 after acquisition by imaging of plural events with a time interval for the same object in the same body.

Figure 16:
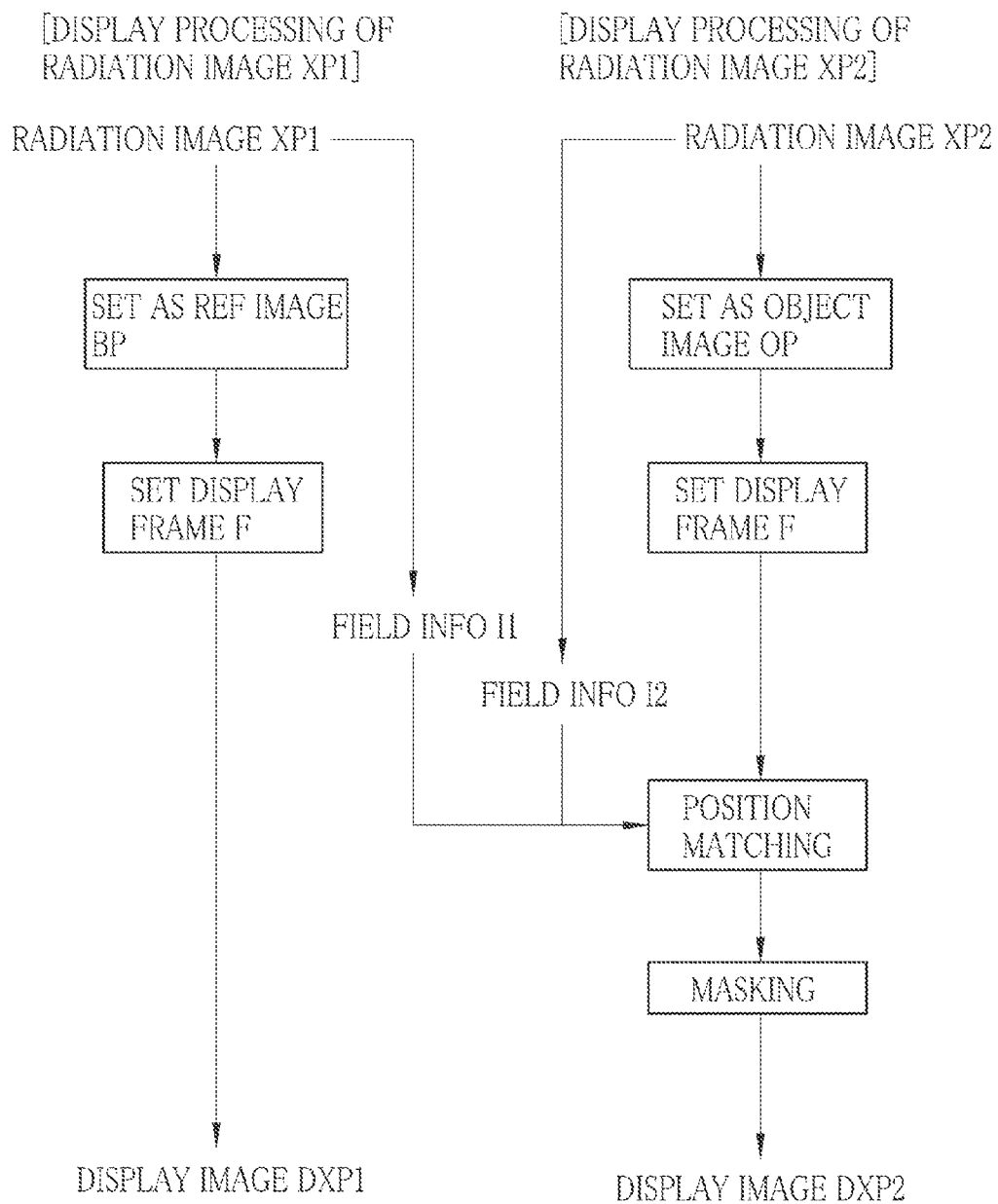
FIG. 16 is a flow chart illustrating display processing of a radiation image.

In FIG. 23, a search query for plural radiation images of the same object in the same body is input through the user input interface 17 for the purpose of observing a progress of the patient. A command signal for position matching is input (yes in the step S20). The information controller 83 retrieves the plural radiation images and field information in compliance with the query. Among the plural retrieved radiation images, one designated as the reference image is transmitted to the user interface controller 82. In FIG. 16, the plural retrieved radiation images and field information of each of the radiation images are transmitted to the matching unit 80 in the step S21.

In FIG. 14A, the user interface controller 82 creates a display image from the radiation image being the reference image BP by simply matching a centerline of the radiation image to the center line of the display frame.

The radiation image designated as the object image OP is processed by the matching unit 80 for the position matching in the method of FIGS. 17 and 18, to set the position of the body in the display image of the object image OP at the position of the body inside the display image of the reference image BP in the step S22. In FIG. 19, the masking unit 81 processes the display image for the masking after the position matching of the object image in the step S23. Thus, the display image of the object image OP can appear with good layout, so image interpretation in comparison can be easily performed. An object in the body of white or gray can be arranged relatively conspicuously with blackening of the masking, to make the body readily recognizable.

The display image of the processed object image OP after being processed in the image processing of the various functions is written to the storage medium 19 in association with the radiation image before the position matching, in the step S24. Therefore, the display image of the processed radiation image stored in the storage medium 19 can be read out for image interpretation after completing the position matching. It is unnecessary to perform the position matching subsequently for each event of image interpretation.

The user interface controller 82 drives the display panel 18 to display the display image of the reference image BP and the display image of the processed object image OP in the comparison window 95 in a comparable manner in the step S25. Assuming that positioning of the body becomes changed at each event of imaging, the position of the exposure field of the plural radiation images is matched by the position matching, so that the image interpretation in comparison can be easy.

As a method of position matching of plural radiation images, a ROI may be designated according to image analysis of output radiation images after the imaging. The ROI may be used as location information for positioning the plural radiation images. In the present embodiment, however, designation of the ROI is made at the time of forming the radiation image by setting the exposure field. The plural radiation images are matched for position matching according to the field information having been already acquired. Thus, time for the position matching can be shortened, because no designation of a ROI is required after outputting radiation images.

As the exposure field set by the field setting unit 56 for the AEC is used for position matching of a plurality of radiation images, utilization of the field information and the technique for automatically setting an exposure field can be effective.

Note that it is conceivable to instruct a user or operator to position a body precisely with strictness in the use of automatically setting an exposure field during irradiation of X-rays. No irregularity in a relative position between the body and the electronic cassette 13 will occur in plural events of imaging for the purpose of observing a progress of the body in diagnosis. Even assuming that a user or operator is instructed to position a body with a strictly high precision, failure in precisely positioning a body may occur with unsuccessful instructions or the like. Automated setting of an exposure field during irradiation of X-rays is advantageous in simple operation of positioning the body, and practically important in a technical point of view. In the present invention, the advantage is to simplify the positioning of the body without excessive precision in the technique of automatically setting an exposure field during the irradiation of X-rays. The feature of position matching according to the field information is utilized for a problem in which a relative position between the body and the electronic cassette 13 may differ.

In case the electronic cassette 13 is set on the floor stand 15 or the patient table 16 for imaging, the positioning can be stable without offset even though the positioning is not very strictly precise, because the object in the body can be positioned by use of a handle bar, chin rest or the like disposed with the floor stand 15 or the patient table 16. Should the electronic cassette 13 be placed on the bed of the patient or manually held by the patient for use, considerable offset may occur in the positioning, because no such useful tool as the handle bar or chin rest is used for positioning. It is concluded that great advantage of the invention can be obtained by the use of the electronic cassette 13 in a separate manner for forming plural radiation images.

In the above embodiment, the position matching is performed by translation for shift on the X-Y plane. However, position matching can be performed by rotation for shift on the X-Y plane, or by rotating the X-Y plane. Let a patient or body be imaged in a posture with an inclination toward the front or the back or a posture with an inclination in a lateral direction for the purpose of imaging a chest of the patient. For this situation, a display image of an object image is rotated for position matching to remove offset, irregularity or the like. It is necessary to use at least two points as reference points of position matching for the purpose of rotation on the X-Y plane. Assuming that exposure fields are determined at right and left lungs, centers of rectangular quadrilaterals tangential externally to the lungs are used as reference points.

In the above embodiment, the method of setting the display frame, the display processing inclusive of the position matching, the various circuit devices and the like are only examples. The invention is not limited to the embodiment. For example, a method of setting the display frame can be setting of coordinates of positions of four side lines around the display frame, and can be setting with an original point of coordinate information and arrangement information relative to the original point, the arrangement information including an area, number of pixels, and the like.

In the above embodiment, plural radiation images formed with time intervals before the observation of the progress are stored in the storage medium 19 of the console structure 14. However, a storage medium separate from the console structure 14 can be used for storing radiation images, for example, an image server connectable to the console structure 14 by network connection. During the observation of the progress, the console structure 14 accesses the image server through the network, and reads out radiation images of interest for the observation.

In the above embodiment, the source and drain in the thin film transistors 43 in the monitoring pixels 41*b* are short-circuited. However, a monitoring pixel can be a pixel of which the photoconductor 42 is directly connected to the signal line 45 without the thin film transistor 43. Also, monitoring pixels 41*c* or detection pixels of an embodiment in FIG. 24 can be used. Elements similar to those of the above embodiment are designated with identical reference numerals.

Figure 24:
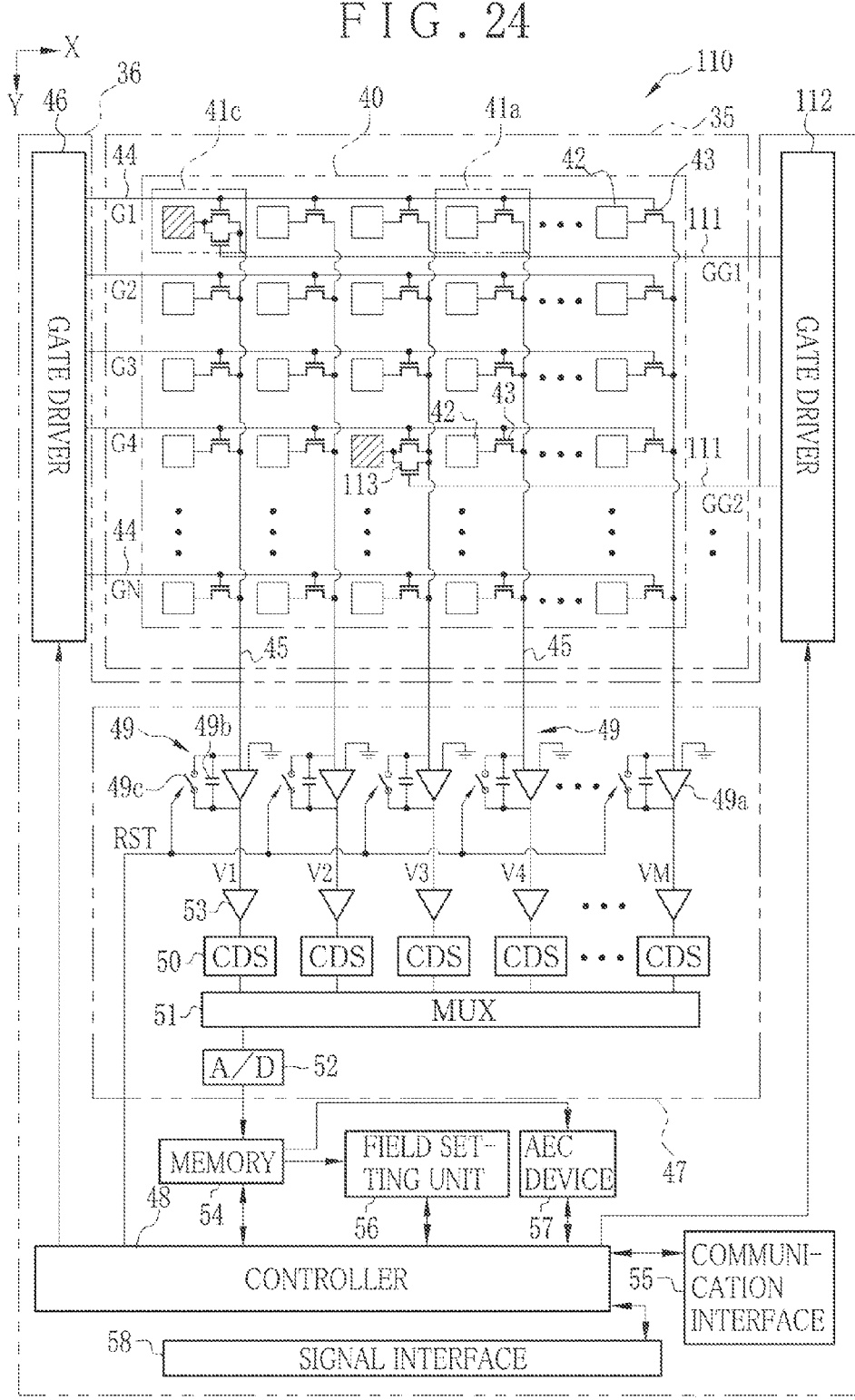
FIG. 24 is a block diagram illustrating another preferred electronic cassette having monitoring pixels of a variant arrangement.

In FIG. 24, a sensor panel 110 includes the monitoring pixels 41*c* having thin film transistors 113 or TFTs in connection. The thin film transistors 113 are driven by a gate driver 112 with a scan line 111, in a distinct manner from the gate driver 46 with the scan lines 44 for driving the thin film transistors 43 in the active pixels 41*a*. It is possible in the monitoring pixels 41*c* to readout charge even while the thin film transistors 43 of the active pixels 41*a* of the same array are turned off for storing, because of connection of the thin film transistors 113.

In the dose monitoring, the gate driver 112 is controlled by the controller 48 to generate gate pulses GG1, GG2, GG3, . . . , GGK (K<N) at a predetermined interval to drive the thin film transistors 113 together in one array, so as to activate the scan line 111 one array after another. The thin film transistors 113 are turned on successively by one array in connection with the scan line 111. Time of the turn-on state is predetermined by a pulse width of the gate pulses. The thin film transistors 113 become turned off upon lapse of the predetermined time of the pulse width. Charge generated by the photoconductors 42 of the monitoring pixels 41*c* becomes drawn into the capacitor 49*b* of the integration amplifier 49 through the signal line 45 while the thin film transistors 113 are turned on irrespective of turning on or off the thin film transistors 43. The charge generated by the monitoring pixels 41*c* and stored in the integration amplifier 49 is output to the A/D converter 52, and digitally converted into a dose signal. The remaining steps are the same as the above-described embodiment.

The sampling period for the dose signal is a period from a start of storing charge in the monitoring pixels 41*c* by turning off the thin film transistors 113 to outputting the stored charge from the monitoring pixels 41*c* to the signal line 45 by inputting a gate pulse to the thin film transistors 113, in short, the period of storing charge in the monitoring pixels 41*c*. In case gate pulses GG1, GG2, GG3, . . . , GGK are input to the thin film transistors 113, dose signals from all of the monitoring pixels 41*b* are written to the memory 54.

Note that it is possible to sample a current in a bias line connected to particular pixels of the sensor panel so as to detect a dose, by utilizing a flow of the current according to charge generated by the pixel in the bias line for supplying bias voltage to the pixel. A dose sensor is constituted by the pixel for monitoring the current of the bias line. Furthermore, it is possible to sample a leak current flowing out of the pixel. A dose sensor is constituted by the pixel for monitoring the leak current. Also, a discrete dose sensor can be provided in an active pixel area in a manner of discretely generating an output with a difference from pixels.

In the above embodiments, the sensor panel has the TFT. However, a sensor panel may be a CMOS type. It is possible in the CMOS type to use a so-called non-destructive readout, in which signal charge is read out as a voltage signal through an amplifier provided in each of the pixels, without flowing the signal charge of pixels to a signal line. Even during the storing, measurement of a dose is possible by selecting given pixels in the active pixel area and reading out the voltage signal of the pixels. The use of the CMOS sensor panel makes it possible to use all the pixels as monitoring pixels in a manner different from the above embodiments in which the monitoring pixels only for the monitoring are provided.

In the above embodiments, the estimated time required for reach of the cumulative dose of the exposure field to the stop threshold is calculated. Upon lapse of the estimated time, the stop signal is transmitted to the source driver. However, the information of the estimated time itself can be transmitted to the source driver. The source driver measures irradiation time of X-rays, and stops the irradiation of X-rays upon reach of the irradiation time to the estimated time. Also, it is possible to compare the cumulative dose of the exposure field with the stop threshold at each time of sampling the dose signal, and to transmit the stop signal to the source driver upon actual reach of the cumulative dose of the exposure field to the stop threshold.

In the above embodiments, X-rays are irradiated in one event for imaging of one event. However, irradiation of X-rays can be performed in two events including pre-irradiation and main irradiation. In the pre-irradiation, a dose of X-rays is set lower than that in the main irradiation. An exposure field is determined according to a dose signal output during the pre-irradiation. Then the AEC in the main irradiation is performed by use of the exposure field set in the pre-irradiation.

In the above embodiments, the position matching and the display of plural radiation images are performed totally by the console structure (user terminal device). However, another user terminal device can be provided with functions of the position matching and the display of plural radiation images in the same manner as the console structure, for example, user terminal device for a doctor or user to perform image diagnosis. Furthermore, only the position matching can be performed in the console structure. A result of the position matching is stored in an image server which can be connected with the console structure and the user terminal device by network connection. The user terminal device can access the image server to read out the result of the position matching. The user terminal device can operate for displaying the plural radiation images. In short, the functions of the position matching, masking and the storage medium can be provided in one multi-function apparatus, or can be provided in plural apparatuses in a discrete manner from one another.

Furthermore, an imaging control unit of a separate type can be used and connected between the electronic cassette and the console structure for performing partial tasks for controlling the electronic cassette in the console structure. In the above embodiments, the electronic cassette is portable. However, an X-ray imaging apparatus of the invention can be an installed type for an imaging stand without portability. In the above embodiments, the radiation is X-rays. However, radiation in the radiographic imaging may be gamma rays or the like.

In the above embodiments, the exposure field A5 may be formed in any shape. However, it is preferable to form the exposure field A5 in a polygonal shape. In the above embodiments, the field information I1 and I2 is constituted by coordinates of a great number of pixels within the exposure field A5. However, other information of pixel addresses of the exposure field A5 can be used. For example, field information can be constituted by coordinates (pixel address) of pixels at vertices of the polygonal shape of a profile line of the exposure field A5. This is advantageous in reducing a data size of the field information.

Furthermore, the feature of the invention can be used in a computer-executable program and a computer-readable storage medium for storing the computer-executable program.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image processing device for image processing of plural radiation images formed by a radiographic imaging apparatus having an active pixel area with plural pixels for detecting a radiation image of a body, said plural radiation images being formed by imaging one object in said body in plural imaging events with a time interval, said radiation image processing device comprising:
    an image acquisition unit for acquiring said radiation images;
    an information controller for obtaining field information of a position of an exposure field which is associated with each one of said radiation images and automatically set in said active pixel area according to a position of said body being positioned for automatic exposure control in said radiographic imaging apparatus before imaging;
    a matching unit for performing position matching according to said field information from said information controller to match said position of said body in said plural radiation images between plural display images corresponding to respectively said plural radiation images.

2. A radiation image processing device as defined in claim 1, wherein said matching unit matches said position of said exposure field between said plural radiation images to match said position of said body between said plural display images.

3. A radiation image processing device as defined in claim 2, wherein said field information is coordinate information of a position of said exposure field in said radiation image.

4. A radiation image processing device as defined in claim 3, wherein said matching unit obtains a reference point of positioning within said exposure field for said position matching.

5. A radiation image processing device as defined in claim 4, wherein said reference point is a center of a quadrilateral frame disposed around said exposure field and tangential to a peripheral line of said exposure field.

6. A radiation image processing device as defined in claim 2, wherein said matching unit selects a reference image from among said plural radiation images, and performs said position matching with reference to a position of said exposure field of said reference image.

7. A radiation image processing device as defined in claim 6, wherein said reference image is one selected radiation image selected among said radiation images by manual or automatic selection.

8. A radiation image processing device as defined in claim 2, wherein said matching unit performs said position matching by shifting an arrangement position of said display image relative to a display frame for arranging said display image.

9. A radiation image processing device as defined in claim 8, further comprising a masking unit for masking of a blank portion formed in said display frame by a shift of said arrangement position.

10. A radiation image processing device as defined in claim 8, further comprising a storage medium for storing an amount of a shift of said display images after said position matching or a shift of said arrangement position in said position matching, in association with said radiation images.

11. A radiation image processing device as defined in claim 1, wherein said field information is expressed by use of pixel addresses of pixels among said pixels corresponding to said exposure field within said radiation images.

12. A radiation image processing device as defined in claim 1, wherein said radiographic imaging apparatus includes:
- a sensor panel having said active pixel area;
- a plurality of monitoring sensors, disposed in said active pixel area discretely from one another, for detecting a dose of radiation incident upon said active pixel area to output a dose signal of said dose;
- a field setting unit for automatically setting said exposure field according to said dose signal from said monitoring sensors during imaging;
- an AEC device for performing said automatic exposure control according to said dose signal from at least one of said monitoring sensors disposed in said exposure field set by said field setting unit.

13. A radiation image processing method of image processing of plural radiation images formed by a radiographic imaging apparatus having an active pixel area with plural pixels for detecting a radiation image of a body, said plural radiation images being formed by imaging one object in said body in plural imaging events with a time interval, said radiation image processing method comprising steps of:
- acquiring said radiation images;
- obtaining field information of a position of an exposure field which is associated with each one of said radiation images and automatically set in said active pixel area according to a position of said body being positioned for automatic exposure control in said radiographic imaging apparatus before imaging;
- performing position matching according to said field information to match said position of said body in said plural radiation images between plural display images corresponding to respectively said plural radiation images.

14. A radiographic imaging system, including a radiographic imaging apparatus having an active pixel area with plural pixels for detecting a radiation image of a body, and a radiation image processing device for image processing of plural radiation images formed by said radiographic imaging apparatus imaging one object in said body in plural imaging events with a time interval, said radiographic imaging system comprising:
- said radiation image processing device including:
  - an image acquisition unit for acquiring said radiation images;
  - an information controller for obtaining field information of a position of an exposure field which is associated with each one of said radiation images and automatically set in said active pixel area according to a position of said body being positioned for automatic exposure control in said radiographic imaging apparatus before imaging;
  - a matching unit for performing position matching according to said field information from said information controller to match said position of said body in said plural radiation images between plural display images corresponding to respectively said plural radiation images.

15. A radiographic imaging system as defined in claim 14, wherein said radiographic imaging apparatus includes:
- a sensor panel having said active pixel area;
- a plurality of monitoring sensors, disposed in said active pixel area discretely from one another, for detecting a dose of radiation incident upon said active pixel area to output a dose signal of said dose;
- a field setting unit for automatically setting said exposure field according to said dose signal from said monitoring sensors during imaging;
- an AEC device for performing said automatic exposure control according to said dose signal from at least one of said monitoring sensors disposed in said exposure field set by said field setting unit.

* * * * *